US010835580B2

(12) United States Patent
Young et al.

(10) Patent No.: US 10,835,580 B2
(45) Date of Patent: Nov. 17, 2020

(54) METHODS COMPRISING CONTINUOUS ADMINISTRATION OF A GLP-1 RECEPTOR AGONIST AND CO-ADMINISTRATION OF A DRUG

(71) Applicant: Intarcia Therapeutics, Inc., Boston, MA (US)

(72) Inventors: Andrew Young, Boston, MA (US); Michelle Baron, Boston, MA (US)

(73) Assignee: INTARCIA THERAPEUTICS, INC., Boston, MA (US)

( * ) Notice: Subject to any disclaimer, the term of this patent is extended or adjusted under 35 U.S.C. 154(b) by 4 days.

(21) Appl. No.: 15/861,258

(22) Filed: Jan. 3, 2018

(65) Prior Publication Data
US 2018/0185451 A1 Jul. 5, 2018

Related U.S. Application Data

(60) Provisional application No. 62/441,833, filed on Jan. 3, 2017.

(51) Int. Cl.
| | | |
|---|---|---|
| *A61K 38/26* | (2006.01) | |
| *A61P 3/04* | (2006.01) | |
| *A61K 9/00* | (2006.01) | |
| *A61P 25/04* | (2006.01) | |
| *A61P 9/00* | (2006.01) | |
| *A61P 25/00* | (2006.01) | |
| *A61K 31/167* | (2006.01) | |
| *A61P 15/18* | (2006.01) | |
| *A61K 31/567* | (2006.01) | |
| *A61K 31/40* | (2006.01) | |
| *A61K 31/7048* | (2006.01) | |
| *A61K 38/05* | (2006.01) | |
| *A61P 7/02* | (2006.01) | |
| *A61K 31/352* | (2006.01) | |
| *A61P 3/10* | (2006.01) | |
| *A61K 31/401* | (2006.01) | |
| *A61K 31/37* | (2006.01) | |
| *A61K 31/565* | (2006.01) | |

(52) U.S. Cl.
CPC ............ *A61K 38/26* (2013.01); *A61K 9/0019* (2013.01); *A61K 9/0053* (2013.01); *A61K 31/167* (2013.01); *A61K 31/352* (2013.01); *A61K 31/37* (2013.01); *A61K 31/40* (2013.01); *A61K 31/401* (2013.01); *A61K 31/565* (2013.01); *A61K 31/567* (2013.01); *A61K 31/7048* (2013.01); *A61K 38/05* (2013.01); *A61P 3/04* (2018.01); *A61P 3/10* (2018.01); *A61P 7/02* (2018.01); *A61P 9/00* (2018.01); *A61P 15/18* (2018.01); *A61P 25/00* (2018.01); *A61P 25/04* (2018.01)

(58) Field of Classification Search
CPC .................................................... A61K 38/26
See application file for complete search history.

(56) References Cited

U.S. PATENT DOCUMENTS

| | | |
|---|---|---|
| 2,110,208 A | 3/1938 | Eggert |
| 2,168,437 A | 8/1939 | Buercklin |
| 2,531,724 A | 11/1950 | Cevasco |
| D179,537 S | 1/1957 | Floyd et al. |
| 3,025,991 A | 3/1962 | Gillon |
| 3,122,162 A | 2/1964 | Sands |
| 3,523,906 A | 8/1970 | Vrancken et al. |
| 3,625,214 A | 12/1971 | Higuchi |
| 3,632,768 A | 1/1972 | Bergy et al. |
| 3,691,090 A | 9/1972 | Kitajima et al. |
| D226,915 S | 5/1973 | Huggins |
| 3,732,865 A | 5/1973 | Higuchi et al. |
| 3,737,337 A | 6/1973 | Schnoring et al. |
| 3,773,919 A | 11/1973 | Boswell et al. |
| 3,797,492 A | 3/1974 | Place |
| 3,869,549 A | 3/1975 | Geller |
| 3,891,570 A | 6/1975 | Fukushima et al. |
| D236,035 S | 7/1975 | Ciencewicki |
| 3,960,757 A | 6/1976 | Morishita et al. |
| 3,987,790 A | 10/1976 | Eckenhoff et al. |
| 3,995,631 A | 12/1976 | Higuchi et al. |
| 3,995,632 A | 12/1976 | Nakano et al. |
| 4,008,719 A | 2/1977 | Theeuwes et al. |
| 4,034,756 A | 7/1977 | Higuchi et al. |
| 4,078,060 A | 3/1978 | Benson et al. |
| 4,111,201 A | 9/1978 | Theeuwes |
| 4,111,202 A | 9/1978 | Theeuwes |
| 4,111,203 A | 9/1978 | Theeuwes |

(Continued)

FOREIGN PATENT DOCUMENTS

| | | |
|---|---|---|
| EP | 0052510 A2 | 5/1982 |
| EP | 0079405 | 5/1983 |

(Continued)

OTHER PUBLICATIONS

Georgios, et al., "Pharmacokinetics and Tolerability of Exenatide Delivered by 7-Day Continuous Subcutaneous Infusion in Healthy Volunteers", Advances in Therapy, Health Communications, Metuchen, NJ, US, vol. 32, No. 7, Jul. 10, 2015, pp. 650-661.

(Continued)

*Primary Examiner* — Gyan Chandra
(74) *Attorney, Agent, or Firm* — Brian C. Trinque; Lathrop GPM

(57) ABSTRACT

Provided is a method for administering to a subject, via an implantable delivery device, a continuous subcutaneous dose of glucagon-like peptide-1 (GLP-1) analog, where the subject is orally co-administered a drug after implantation of the implantable delivery device and during continuous subcutaneous dosing of the GLP-1 analog.

29 Claims, 11 Drawing Sheets

Specification includes a Sequence Listing.

(56) References Cited

U.S. PATENT DOCUMENTS

| | | |
|---|---|---|
| 4,203,439 A | 5/1980 | Theeuwes |
| 4,211,771 A | 7/1980 | Witkowski et al. |
| 4,221,862 A | 9/1980 | Naito et al. |
| 4,243,030 A | 1/1981 | Lynch et al. |
| D258,837 S | 4/1981 | Spranger et al. |
| D259,458 S | 6/1981 | Fuller et al. |
| 4,305,927 A | 12/1981 | Theeuwes et al. |
| 4,310,516 A | 1/1982 | Chang et al. |
| 4,340,054 A | 7/1982 | Michaels |
| 4,350,271 A | 9/1982 | Eckenhoff |
| 4,373,527 A | 2/1983 | Fischell |
| 4,376,118 A | 3/1983 | Daher |
| 4,384,975 A | 5/1983 | Fong |
| 4,389,330 A | 6/1983 | Tice et al. |
| 4,439,196 A | 3/1984 | Higuchi |
| 4,444,498 A | 4/1984 | Heinemann |
| 4,455,143 A | 6/1984 | Theeuwes et al. |
| 4,455,145 A | 6/1984 | Theeuwes |
| 4,530,840 A | 7/1985 | Tice et al. |
| 4,552,561 A | 11/1985 | Eckenhoff et al. |
| 4,588,614 A | 5/1986 | Lauchenauer |
| 4,594,108 A | 6/1986 | Greminger, Jr. et al. |
| 4,609,374 A | 9/1986 | Ayer |
| 4,639,244 A | 1/1987 | Rizk et al. |
| 4,655,462 A | 4/1987 | Balsells |
| 4,673,405 A | 6/1987 | Guittard et al. |
| 4,675,184 A | 6/1987 | Hasegawa et al. |
| 4,695,623 A | 9/1987 | Stabinsky |
| 4,727,138 A | 2/1988 | Goeddel et al. |
| 4,734,284 A | 3/1988 | Terada et al. |
| 4,737,437 A | 4/1988 | Gutsell, Jr. et al. |
| 4,743,449 A | 5/1988 | Yoshida et al. |
| 4,753,651 A | 6/1988 | Eckenhoff |
| 4,762,791 A | 8/1988 | Goeddel et al. |
| 4,765,989 A | 8/1988 | Wong et al. |
| 4,783,337 A | 11/1988 | Wong et al. |
| 4,818,517 A | 4/1989 | Kwee et al. |
| 4,820,638 A | 4/1989 | Swetly et al. |
| 4,826,144 A | 5/1989 | Balsells |
| 4,830,344 A | 5/1989 | Balsells |
| 4,840,896 A | 6/1989 | Reddy et al. |
| 4,845,196 A | 7/1989 | Cowling |
| 4,847,079 A | 7/1989 | Kwan |
| 4,851,228 A | 7/1989 | Zentner et al. |
| 4,865,845 A | 9/1989 | Eckenhoff et al. |
| 4,873,080 A | 10/1989 | Brickl et al. |
| 4,874,388 A | 10/1989 | Wong et al. |
| 4,876,781 A | 10/1989 | Balsells |
| 4,885,166 A | 12/1989 | Meyer et al. |
| 4,886,668 A | 12/1989 | Haslam et al. |
| 4,892,778 A | 1/1990 | Theeuwes et al. |
| 4,893,795 A | 1/1990 | Balsells |
| 4,897,471 A | 1/1990 | Stabinsky |
| 4,907,788 A | 3/1990 | Balsells |
| 4,915,366 A | 4/1990 | Balsells |
| 4,915,949 A | 4/1990 | Wong et al. |
| 4,915,954 A | 4/1990 | Ayer et al. |
| 4,917,887 A | 4/1990 | Hauptmann et al. |
| 4,917,895 A | 4/1990 | Lee et al. |
| 4,923,805 A | 5/1990 | Reddy et al. |
| 4,927,687 A | 5/1990 | Nuwayser |
| 4,929,554 A | 5/1990 | Goeddel et al. |
| 4,931,285 A | 6/1990 | Edgren et al. |
| 4,934,666 A | 6/1990 | Balsells |
| 4,940,465 A | 7/1990 | Theeuwes et al. |
| 4,940,588 A | 7/1990 | Sparks et al. |
| 4,952,402 A | 8/1990 | Sparks et al. |
| 4,957,119 A | 9/1990 | de Nijs |
| 4,961,253 A | 10/1990 | Balsells |
| 4,964,204 A | 10/1990 | Balsells |
| 4,969,884 A | 11/1990 | Yum |
| 4,974,821 A | 12/1990 | Balsells |
| 4,976,966 A | 12/1990 | Theeuwes et al. |
| 5,004,689 A | 4/1991 | Fiers et al. |
| 5,006,346 A | 4/1991 | Theeuwes et al. |
| 5,019,382 A | 5/1991 | Cummins, Jr. |
| 5,019,400 A | 5/1991 | Gombotz et al. |
| 5,023,088 A | 6/1991 | Wong et al. |
| 5,024,842 A | 6/1991 | Edgren et al. |
| 5,030,216 A | 7/1991 | Theeuwes et al. |
| 5,034,229 A | 7/1991 | Magruder et al. |
| 5,057,318 A | 10/1991 | Magruder et al. |
| 5,059,423 A | 10/1991 | Magruder et al. |
| 5,066,436 A | 11/1991 | Komen et al. |
| 5,071,642 A | 12/1991 | Lahr et al. |
| 5,072,070 A | 12/1991 | Balsells |
| 5,079,388 A | 1/1992 | Balsells |
| 5,091,188 A | 2/1992 | Haynes |
| 5,108,078 A | 4/1992 | Balsells |
| 5,110,596 A | 5/1992 | Magruder et al. |
| 5,112,614 A | 5/1992 | Magruder et al. |
| 5,113,938 A | 5/1992 | Clayton |
| 5,117,066 A | 5/1992 | Balsells |
| D326,718 S | 6/1992 | Maxwell |
| 5,118,666 A | 6/1992 | Habener |
| 5,120,306 A | 6/1992 | Gosselin |
| 5,120,712 A | 6/1992 | Habener |
| 5,120,832 A | 6/1992 | Goeddel et al. |
| 5,122,128 A | 6/1992 | Cardinal et al. |
| 5,122,377 A | 6/1992 | Miller |
| 5,126,142 A | 6/1992 | Ayer et al. |
| 5,126,147 A | 6/1992 | Silvestri et al. |
| 5,134,244 A | 7/1992 | Balsells |
| 5,137,727 A | 8/1992 | Eckenhoff |
| D329,278 S | 9/1992 | Gallup |
| 5,151,093 A | 9/1992 | Theeuwes et al. |
| 5,160,122 A | 11/1992 | Balsells |
| 5,160,743 A | 11/1992 | Edgren et al. |
| 5,161,806 A | 11/1992 | Balsells |
| 5,180,591 A | 1/1993 | Margruder et al. |
| 5,190,765 A | 3/1993 | Jao et al. |
| 5,203,849 A | 4/1993 | Balsells |
| 5,204,108 A | 4/1993 | Illum |
| 5,207,752 A | 5/1993 | Sorensen et al. |
| 5,209,746 A | 5/1993 | Balaban et al. |
| 5,213,809 A | 5/1993 | Wright et al. |
| 5,213,810 A | 5/1993 | Steber |
| 5,219,572 A | 6/1993 | Sivaramakrishnan |
| 5,221,278 A | 6/1993 | Linkwitz et al. |
| 5,223,265 A | 6/1993 | Wong |
| 5,225,205 A | 7/1993 | Orsolini |
| 5,231,176 A | 7/1993 | Goeddel et al. |
| 5,234,424 A | 8/1993 | Yum et al. |
| 5,234,692 A | 8/1993 | Magruder et al. |
| 5,234,693 A | 8/1993 | Magruder et al. |
| 5,234,695 A | 8/1993 | Hobbs et al. |
| 5,252,338 A | 10/1993 | Jao et al. |
| 5,260,069 A | 11/1993 | Chen |
| D342,855 S | 1/1994 | Butler, II |
| 5,278,151 A | 1/1994 | Korb et al. |
| 5,279,608 A | 1/1994 | Cherif Cheikh |
| 5,284,655 A | 2/1994 | Bogdansky et al. |
| 5,288,501 A | 2/1994 | Nürnberg et al. |
| 5,288,502 A | 2/1994 | Mcginity et al. |
| 5,290,271 A | 3/1994 | Jernberg |
| 5,300,079 A | 4/1994 | Niezink et al. |
| 5,300,302 A | 4/1994 | Tachon et al. |
| 5,308,348 A | 5/1994 | Balaban et al. |
| 5,312,335 A | 5/1994 | McKinnon et al. |
| 5,312,389 A | 5/1994 | Theeuwes et al. |
| 5,312,390 A | 5/1994 | Wong |
| 5,318,558 A | 6/1994 | Linkwitz et al. |
| 5,318,780 A | 6/1994 | Viegas et al. |
| 5,320,616 A | 6/1994 | Magruder et al. |
| 5,324,280 A | 6/1994 | Wong et al. |
| 5,336,057 A | 8/1994 | Fukuda et al. |
| 5,336,505 A | 8/1994 | Ng et al. |
| 5,352,662 A | 10/1994 | Brooks et al. |
| 5,368,588 A | 11/1994 | Bettinger |
| 5,368,863 A | 11/1994 | Eckenhoff et al. |
| 5,371,089 A | 12/1994 | Rattan |
| 5,374,620 A | 12/1994 | Clark et al. |
| 5,385,738 A | 1/1995 | Yamahira et al. |
| 5,385,887 A | 1/1995 | Yim et al. |

(56) References Cited

U.S. PATENT DOCUMENTS

| | | |
|---|---|---|
| 5,407,609 A | 4/1995 | Tice et al. |
| D358,644 S | 5/1995 | Park |
| 5,411,951 A | 5/1995 | Mitchell |
| 5,413,572 A | 5/1995 | Wong et al. |
| 5,413,672 A | 5/1995 | Hirotsuji et al. |
| 5,424,286 A | 6/1995 | Eng |
| 5,428,024 A | 6/1995 | Chu et al. |
| 5,429,602 A | 7/1995 | Hauser |
| 5,439,688 A | 8/1995 | Orsolini et al. |
| 5,443,459 A | 8/1995 | Wong et al. |
| 5,445,829 A | 8/1995 | Paradissis et al. |
| 5,456,679 A | 10/1995 | Balaban et al. |
| 5,458,888 A | 10/1995 | Chen |
| 5,464,929 A | 11/1995 | Bezwada et al. |
| 5,472,708 A | 12/1995 | Chen |
| 5,478,564 A | 12/1995 | Wantier et al. |
| 5,486,365 A | 1/1996 | Takado et al. |
| 5,498,255 A | 3/1996 | Wong et al. |
| 5,511,355 A | 4/1996 | Dingler |
| 5,512,293 A | 4/1996 | Landrau et al. |
| 5,512,549 A | 4/1996 | Chen et al. |
| 5,514,110 A | 5/1996 | Teh |
| 5,529,914 A | 6/1996 | Hubbell et al. |
| 5,531,736 A | 7/1996 | Wong et al. |
| 5,540,665 A | 7/1996 | Mercado et al. |
| 5,540,912 A | 7/1996 | Roorda et al. |
| 5,541,172 A | 7/1996 | Labrie et al. |
| 5,542,682 A | 8/1996 | Goldstein et al. |
| 5,543,156 A | 8/1996 | Roorda et al. |
| 5,545,618 A | 8/1996 | Buckley et al. |
| 5,556,642 A | 9/1996 | Kobayashi et al. |
| 5,557,318 A | 9/1996 | Gabriel |
| 5,571,525 A | 11/1996 | Roorda et al. |
| 5,574,008 A | 11/1996 | Johnson et al. |
| 5,574,137 A | 11/1996 | Gray et al. |
| 5,580,578 A | 12/1996 | Oshlack et al. |
| 5,589,167 A | 12/1996 | Cleland et al. |
| 5,595,751 A | 1/1997 | Bezwada |
| 5,595,759 A | 1/1997 | Wright et al. |
| 5,597,579 A | 1/1997 | Bezwada et al. |
| 5,602,010 A | 2/1997 | Hauptmann et al. |
| 5,605,688 A | 2/1997 | Himmler et al. |
| 5,607,687 A | 3/1997 | Bezwada et al. |
| 5,609,885 A | 3/1997 | Rivera et al. |
| 5,614,221 A | 3/1997 | Fjellstrom |
| 5,614,492 A | 3/1997 | Habener |
| 5,618,552 A | 4/1997 | Bezwada et al. |
| 5,620,698 A | 4/1997 | Bezwada et al. |
| 5,620,705 A | 4/1997 | Dong et al. |
| 5,630,796 A | 5/1997 | Bellhouse et al. |
| 5,633,011 A | 5/1997 | Dong et al. |
| 5,635,213 A | 6/1997 | Nystrom et al. |
| 5,639,477 A | 6/1997 | Maruyama et al. |
| 5,639,640 A | 6/1997 | Reddy et al. |
| 5,645,850 A | 7/1997 | Bezwada et al. |
| 5,648,088 A | 7/1997 | Bezwada et al. |
| 5,650,173 A | 7/1997 | Ramstack et al. |
| 5,654,008 A | 8/1997 | Herbert et al. |
| 5,654,010 A | 8/1997 | Johnson et al. |
| 5,656,297 A | 8/1997 | Bernstein et al. |
| 5,656,299 A | 8/1997 | Kino et al. |
| 5,658,593 A | 8/1997 | Orly et al. |
| 5,660,847 A | 8/1997 | Magruder et al. |
| 5,660,858 A | 8/1997 | Parikh et al. |
| 5,660,861 A | 8/1997 | Jao et al. |
| 5,667,808 A | 9/1997 | Johnson et al. |
| 5,668,170 A | 9/1997 | Gyory |
| 5,672,549 A | 9/1997 | Minami et al. |
| 5,676,942 A | 10/1997 | Testa et al. |
| 5,686,097 A | 11/1997 | Taskovich et al. |
| 5,688,801 A | 11/1997 | Mesens et al. |
| 5,690,925 A | 11/1997 | Gray et al. |
| 5,690,952 A | 11/1997 | Magruder et al. |
| 5,697,113 A | 12/1997 | Shatz et al. |
| 5,698,213 A | 12/1997 | Jamiolkowski et al. |
| 5,700,486 A | 12/1997 | Canal et al. |
| 5,700,583 A | 12/1997 | Jamiolkowski et al. |
| 5,703,200 A | 12/1997 | Bezwada et al. |
| 5,707,644 A | 1/1998 | Illum |
| 5,711,967 A | 1/1998 | Juch |
| 5,713,847 A | 2/1998 | Howard, III et al. |
| 5,718,922 A | 2/1998 | Herrero-Vanrell |
| 5,728,088 A | 3/1998 | Margruder et al. |
| 5,728,396 A | 3/1998 | Peery et al. |
| 5,733,572 A | 3/1998 | Unger et al. |
| 5,736,159 A | 4/1998 | Chen et al. |
| 5,738,845 A | 4/1998 | Imakawa |
| 5,747,058 A | 5/1998 | Tipton et al. |
| 5,756,450 A | 5/1998 | Hahn et al. |
| 5,767,251 A | 6/1998 | Reddy et al. |
| 5,770,231 A | 6/1998 | Mesens et al. |
| 5,782,396 A | 7/1998 | Mastri et al. |
| 5,792,477 A | 8/1998 | Rickey et al. |
| 5,795,591 A | 8/1998 | Lee et al. |
| 5,795,779 A | 8/1998 | McCormick et al. |
| 5,807,876 A | 9/1998 | Armistead et al. |
| 5,814,323 A | 9/1998 | Lyle |
| D399,821 S | 10/1998 | Tyneski et al. |
| 5,817,129 A | 10/1998 | Labrecque et al. |
| 5,830,501 A | 11/1998 | Dong et al. |
| 5,836,935 A | 11/1998 | Ashton et al. |
| 5,843,891 A | 12/1998 | Sherman |
| 5,844,017 A | 12/1998 | Jamiolkowski et al. |
| 5,851,451 A | 12/1998 | Takechi et al. |
| 5,858,746 A | 1/1999 | Hubbell et al. |
| 5,859,150 A | 1/1999 | Jamiolkowski et al. |
| 5,861,166 A | 1/1999 | Eckenhoff |
| 5,871,770 A | 2/1999 | Margruder et al. |
| 5,871,778 A | 2/1999 | Kino et al. |
| 5,874,388 A | 2/1999 | Hsu |
| 5,876,746 A | 3/1999 | Jona et al. |
| 5,882,676 A | 3/1999 | Lee et al. |
| D408,917 S | 4/1999 | Hacker |
| 5,904,935 A | 5/1999 | Eckenhoff et al. |
| 5,906,816 A | 5/1999 | Soos et al. |
| 5,906,830 A | 5/1999 | Farinas et al. |
| 5,908,621 A | 6/1999 | Glue et al. |
| 5,916,598 A | 6/1999 | Rickey et al. |
| 5,922,253 A | 7/1999 | Herbert et al. |
| 5,928,666 A | 7/1999 | Farinas et al. |
| 5,932,547 A | 8/1999 | Stevenson et al. |
| 5,938,654 A | 8/1999 | Wong et al. |
| 5,939,286 A | 8/1999 | Johnson et al. |
| 5,942,223 A | 8/1999 | Bazer et al. |
| 5,942,253 A | 8/1999 | Gombotz et al. |
| 5,945,126 A | 8/1999 | Thanoo et al. |
| 5,948,430 A | 9/1999 | Zerbe et al. |
| 5,958,909 A | 9/1999 | Habener |
| D415,073 S | 10/1999 | Meehan et al. |
| 5,962,023 A | 10/1999 | Jamiolkowski et al. |
| 5,965,168 A | 10/1999 | Mesens et al. |
| 5,972,370 A | 10/1999 | Eckenhoff et al. |
| 5,972,373 A | 10/1999 | Yajima et al. |
| 5,976,109 A | 11/1999 | Heruth |
| 5,980,945 A | 11/1999 | Ruiz |
| 5,981,719 A | 11/1999 | Woiszwillo et al. |
| 5,984,890 A | 11/1999 | Gast et al. |
| 5,985,305 A | 11/1999 | Peery et al. |
| 5,989,463 A | 11/1999 | Tracy et al. |
| 5,997,527 A | 12/1999 | Gumucio et al. |
| 5,997,902 A | 12/1999 | Maruyama et al. |
| 6,007,805 A | 12/1999 | Foster et al. |
| 6,017,545 A | 1/2000 | Modi |
| 6,022,561 A | 2/2000 | Carlsson et al. |
| 6,023,802 A | 2/2000 | King |
| 6,029,361 A | 2/2000 | Newman |
| 6,056,718 A | 5/2000 | Funderburk et al. |
| 6,060,450 A | 5/2000 | Soos et al. |
| 6,069,133 A | 5/2000 | Carlo et al. |
| 6,074,660 A | 6/2000 | Jamiolkowski et al. |
| 6,074,673 A | 6/2000 | Guillen |
| 6,100,346 A | 8/2000 | Jamiolkowski et al. |
| 6,110,503 A | 8/2000 | Rickey et al. |
| 6,113,938 A | 9/2000 | Chen et al. |

(56) References Cited

U.S. PATENT DOCUMENTS

| | | |
|---|---|---|
| 6,113,947 A | 9/2000 | Cleland et al. |
| 6,120,787 A | 9/2000 | Gustafsson et al. |
| 6,124,261 A | 9/2000 | Stevenson et al. |
| 6,124,281 A | 9/2000 | Lewis et al. |
| 6,127,520 A | 10/2000 | Ueda et al. |
| 6,129,761 A | 10/2000 | Hubbell |
| 6,130,200 A | 10/2000 | Brodbeck et al. |
| 6,132,420 A | 10/2000 | Dionne et al. |
| 6,133,249 A | 10/2000 | Hills |
| 6,133,429 A | 10/2000 | Davis et al. |
| 6,147,168 A | 11/2000 | Jamiolkowski et al. |
| 6,156,331 A | 12/2000 | Peery et al. |
| 6,172,046 B1 | 1/2001 | Albrecht |
| 6,174,547 B1 | 1/2001 | Dong et al. |
| 6,177,096 B1 | 1/2001 | Zerbe et al. |
| 6,183,461 B1 | 2/2001 | Matsuura et al. |
| 6,187,095 B1 | 2/2001 | Labrecque et al. |
| 6,190,350 B1 | 2/2001 | Davis et al. |
| 6,190,700 B1 | 2/2001 | Okada et al. |
| 6,190,702 B1 | 2/2001 | Takada et al. |
| 6,191,102 B1 | 2/2001 | DiMarchi et al. |
| 6,204,022 B1 | 3/2001 | Johnson et al. |
| 6,217,893 B1 | 4/2001 | Pellet et al. |
| 6,217,906 B1 | 4/2001 | Gumucio et al. |
| 6,217,908 B1 | 4/2001 | Mathiowitz et al. |
| 6,218,431 B1 | 4/2001 | Schoen et al. |
| 6,224,894 B1 | 5/2001 | Jamiolkowski et al. |
| 6,235,712 B1 | 5/2001 | Stevenson et al. |
| 6,245,349 B1 | 6/2001 | Yiv et al. |
| 6,245,357 B1 | 6/2001 | Edgren et al. |
| 6,248,112 B1 | 6/2001 | Gambale et al. |
| 6,251,435 B1 | 6/2001 | Jamiolkowski et al. |
| D445,975 S | 7/2001 | Stratford |
| 6,258,377 B1 | 7/2001 | New et al. |
| 6,261,584 B1 | 7/2001 | Peery et al. |
| 6,268,343 B1 | 7/2001 | Knudsen et al. |
| 6,270,700 B1 | 8/2001 | Ignatious |
| 6,270,787 B1 | 8/2001 | Ayer |
| 6,277,413 B1 | 8/2001 | Sankaram |
| 6,283,949 B1 | 9/2001 | Roorda |
| 6,284,264 B1 | 9/2001 | Zerbe et al. |
| 6,284,725 B1 | 9/2001 | Coolidge et al. |
| 6,284,727 B1 | 9/2001 | Kim et al. |
| 6,287,295 B1 | 9/2001 | Chen et al. |
| 6,329,336 B1 | 12/2001 | Bridon et al. |
| 6,331,311 B1 | 12/2001 | Brodbeck et al. |
| 6,372,218 B1 | 4/2002 | Cummins, Jr. |
| 6,372,256 B2 | 4/2002 | Jamiolkowski et al. |
| 6,375,978 B1 | 4/2002 | Kleiner et al. |
| 6,395,292 B2 | 5/2002 | Peery et al. |
| 6,403,655 B1 | 6/2002 | Bezwada et al. |
| 6,419,952 B2 | 7/2002 | Wong et al. |
| 6,433,144 B1 | 8/2002 | Morris et al. |
| 6,436,091 B1 | 8/2002 | Harper et al. |
| 6,447,522 B2 | 9/2002 | Gambale et al. |
| 6,451,974 B1 | 9/2002 | Hansen |
| 6,458,385 B2 | 10/2002 | Jamiolkowski et al. |
| 6,458,387 B1 | 10/2002 | Scott et al. |
| 6,458,924 B2 | 10/2002 | Knudsen et al. |
| 6,461,605 B1 | 10/2002 | Cutler et al. |
| 6,464,688 B1 | 10/2002 | Harper et al. |
| 6,468,961 B1 | 10/2002 | Brodbeck et al. |
| 6,471,688 B1 | 10/2002 | Harper et al. |
| 6,472,512 B1 | 10/2002 | LaFleur et al. |
| 6,485,706 B1 | 11/2002 | McCoy et al. |
| 6,495,164 B1 | 12/2002 | Ramstack et al. |
| 6,506,724 B1 | 1/2003 | Hiles et al. |
| 6,508,808 B1 | 1/2003 | Carr et al. |
| 6,514,500 B1 | 2/2003 | Bridon et al. |
| 6,514,517 B2 | 2/2003 | Jamilolkowski et al. |
| 6,524,305 B1 | 2/2003 | Peterson et al. |
| 6,528,093 B1 | 3/2003 | Kamei et al. |
| 6,528,486 B1 | 3/2003 | Larsen et al. |
| D472,896 S | 4/2003 | Peiker |
| 6,541,021 B1 | 4/2003 | Johnson et al. |
| 6,544,252 B1 | 4/2003 | Theeuwes et al. |
| 6,547,250 B1 | 4/2003 | Noble |
| 6,551,613 B1 | 4/2003 | Dong et al. |
| 6,569,420 B2 | 5/2003 | Chen et al. |
| 6,572,890 B2 | 6/2003 | Faour et al. |
| 6,579,851 B2 | 6/2003 | Goeke et al. |
| 6,592,887 B2 | 7/2003 | Zerbe et al. |
| 6,593,295 B2 | 7/2003 | Bridon et al. |
| 6,635,268 B2 | 10/2003 | Peery et al. |
| 6,667,061 B2 | 12/2003 | Ramstack et al. |
| 6,670,368 B1 | 12/2003 | Breault et al. |
| 6,673,767 B1 | 1/2004 | Brodbeck et al. |
| 6,682,522 B2 | 1/2004 | Carr et al. |
| 6,703,225 B1 | 3/2004 | Kojima et al. |
| 6,703,359 B1 | 3/2004 | Young et al. |
| 6,706,689 B2 | 3/2004 | Coolidge et al. |
| 6,709,671 B2 | 3/2004 | Zerbe et al. |
| 6,720,407 B1 | 4/2004 | Hughes et al. |
| 6,730,328 B2 | 5/2004 | Maskiwicz et al. |
| 6,767,887 B1 | 7/2004 | Hoffmann et al. |
| 6,821,949 B2 | 11/2004 | Bridon et al. |
| 6,833,256 B1 | 12/2004 | Pontzer et al. |
| 6,835,194 B2 | 12/2004 | Johnson et al. |
| 6,840,931 B2 | 1/2005 | Peterson et al. |
| 6,849,708 B1 | 2/2005 | Habener |
| 6,849,714 B1 | 2/2005 | Bridon et al. |
| 6,858,576 B1 | 2/2005 | Young et al. |
| 6,872,700 B1 | 3/2005 | Young et al. |
| 6,875,748 B2 | 4/2005 | Manthorpe et al. |
| 6,887,470 B1 | 5/2005 | Bridon et al. |
| 6,887,849 B2 | 5/2005 | Bridon et al. |
| 6,899,887 B2 | 5/2005 | Ayer |
| 6,899,898 B2 | 5/2005 | Albayrak |
| 6,902,744 B1 | 6/2005 | Kolterman et al. |
| 6,903,186 B1 | 6/2005 | Dong |
| 6,913,767 B1 | 7/2005 | Cleland et al. |
| 6,923,800 B2 | 8/2005 | Chen et al. |
| 6,924,264 B1 | 8/2005 | Prickett et al. |
| 6,939,556 B2 | 9/2005 | Lautenbach |
| 6,956,026 B2 | 10/2005 | Beeley et al. |
| 6,969,702 B2 | 11/2005 | Bertilsson et al. |
| 6,976,981 B2 | 12/2005 | Ayer |
| 6,989,366 B2 | 1/2006 | Beeley et al. |
| 6,992,065 B2 | 1/2006 | Okumu |
| 6,997,922 B2 | 2/2006 | Theeuwes et al. |
| 7,014,636 B2 | 3/2006 | Gilbert |
| 7,022,674 B2 | 4/2006 | DeFelippis et al. |
| 7,041,646 B2 | 5/2006 | Pan et al. |
| 7,074,423 B2 | 7/2006 | Fereira et al. |
| 7,084,243 B2 | 8/2006 | Glaesner et al. |
| 7,101,567 B1 | 9/2006 | Sano et al. |
| 7,101,843 B2 | 9/2006 | Glaesner et al. |
| 7,112,335 B2 | 9/2006 | Lautenbach |
| 7,115,569 B2 | 10/2006 | Beeley et al. |
| 7,138,375 B2 | 11/2006 | Beeley et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,153,825 B2 | 12/2006 | Young et al. |
| 7,157,555 B1 | 1/2007 | Beeley et al. |
| 7,163,688 B2 | 1/2007 | Peery et al. |
| 7,163,697 B2 | 1/2007 | Hanes et al. |
| 7,199,217 B2 | 4/2007 | DiMarchi et al. |
| 7,205,409 B2 | 4/2007 | Pei et al. |
| 7,207,982 B2 | 4/2007 | Dionne et al. |
| 7,241,457 B2 | 7/2007 | Chen et al. |
| 7,258,869 B1 | 8/2007 | Berry et al. |
| D555,589 S | 11/2007 | Hussaini et al. |
| 7,297,761 B2 | 11/2007 | Beeley et al. |
| 7,316,680 B2 | 1/2008 | Gilbert |
| 7,393,827 B2 | 7/2008 | Nadler |
| 7,407,499 B2 | 8/2008 | Trautman |
| 7,442,682 B2 | 10/2008 | Kitaura et al. |
| 7,456,254 B2 | 11/2008 | Wright et al. |
| 7,459,432 B2 | 12/2008 | Cowley et al. |
| 7,521,423 B2 | 4/2009 | Young et al. |
| 7,563,871 B2 | 7/2009 | Wright et al. |
| 7,589,169 B2 | 9/2009 | Bolotin |
| 7,612,176 B2 | 11/2009 | Wright et al. |

(56) References Cited

U.S. PATENT DOCUMENTS

| | | |
|---|---|---|
| 7,635,463 B2 | 12/2009 | Bolotin et al. |
| D608,447 S | 1/2010 | Meyer et al. |
| 7,655,254 B2 | 2/2010 | Dennis et al. |
| 7,655,257 B2 | 2/2010 | Peery et al. |
| 7,666,835 B2 | 2/2010 | Bloom et al. |
| 7,682,356 B2 | 3/2010 | Alessi et al. |
| 7,727,519 B2 | 6/2010 | Moran |
| 7,731,947 B2 | 6/2010 | Eliaz et al. |
| 7,736,665 B2 | 6/2010 | Patel et al. |
| 7,741,269 B2 | 6/2010 | Young et al. |
| 7,790,140 B2 | 9/2010 | Bolotin |
| 7,825,091 B2 | 11/2010 | Bloom et al. |
| 7,829,109 B2 | 11/2010 | Chen et al. |
| 7,833,543 B2 | 11/2010 | Gibson et al. |
| 7,879,028 B2 | 2/2011 | Alessi et al. |
| 7,879,794 B2 | 2/2011 | Weyer et al. |
| 7,919,109 B2 | 4/2011 | Berry et al. |
| 7,928,065 B2 | 4/2011 | Young et al. |
| D638,478 S | 5/2011 | Block |
| 7,959,938 B2 | 6/2011 | Rohloff et al. |
| 7,964,183 B2 | 6/2011 | Eliaz et al. |
| 8,039,432 B2 | 10/2011 | Bridon et al. |
| 8,048,438 B2 | 11/2011 | Berry et al. |
| 8,052,996 B2 | 11/2011 | Lautenbach et al. |
| 8,058,233 B2 | 11/2011 | Cowley et al. |
| 8,101,576 B2 | 1/2012 | Bloom |
| 8,114,430 B2 | 2/2012 | Rohloff et al. |
| 8,114,437 B2 | 2/2012 | Rohloff et al. |
| 8,158,150 B2 | 4/2012 | Lautenbach et al. |
| 8,173,150 B2 | 5/2012 | Berry et al. |
| 8,202,836 B2 | 6/2012 | Moore et al. |
| 8,206,745 B2 | 6/2012 | Rohloff et al. |
| 8,211,467 B2 | 7/2012 | Rohloff et al. |
| 8,217,001 B2 | 7/2012 | Cowley et al. |
| 8,231,859 B2 | 7/2012 | Bolotin et al. |
| 8,257,682 B2 | 9/2012 | Bolotin et al. |
| 8,257,691 B2 | 9/2012 | Eliaz et al. |
| 8,262,667 B1 | 9/2012 | Silver et al. |
| 8,263,545 B2 | 9/2012 | Levy et al. |
| 8,263,736 B2 | 9/2012 | Berry |
| 8,268,341 B2 | 9/2012 | Berry |
| 8,273,365 B2 | 9/2012 | Lautenbach et al. |
| 8,273,713 B2 | 9/2012 | Pittner et al. |
| D669,589 S | 10/2012 | Delaey |
| 8,277,776 B2 | 10/2012 | Bolotin et al. |
| 8,278,267 B2 | 10/2012 | Weyer et al. |
| 8,288,338 B2 | 10/2012 | Young et al. |
| 8,298,561 B2 | 10/2012 | Alessi et al. |
| 8,299,025 B2 | 10/2012 | Alessi et al. |
| 8,343,140 B2 | 1/2013 | Alessi et al. |
| 8,367,095 B2 | 2/2013 | Lautenbach et al. |
| 8,372,424 B2 | 2/2013 | Berry et al. |
| D678,889 S | 3/2013 | Chiu |
| 8,398,967 B2 | 3/2013 | Eliaz et al. |
| 8,440,226 B2 | 5/2013 | Rohloff et al. |
| 8,460,694 B2 | 6/2013 | Rohloff et al. |
| 8,470,353 B2 | 6/2013 | Lautenbach et al. |
| 8,801,700 B2 | 8/2014 | Alessi et al. |
| 8,815,802 B2 | 8/2014 | Kalthoff et al. |
| 8,858,621 B2 | 10/2014 | Oba et al. |
| 8,865,202 B2 | 10/2014 | Zerbe et al. |
| 8,888,745 B2 | 11/2014 | Van Der Graaf et al. |
| 8,926,595 B2 | 1/2015 | Alessi et al. |
| 8,940,316 B2 | 1/2015 | Alessi et al. |
| 8,992,961 B2 | 3/2015 | Berry et al. |
| 8,992,962 B2 | 3/2015 | Lautenbach et al. |
| 9,044,209 B2 | 6/2015 | Dayton et al. |
| 9,078,900 B2 | 7/2015 | Kuzma et al. |
| 9,095,553 B2 | 8/2015 | Rohloff et al. |
| 9,241,722 B2 | 1/2016 | Yu |
| D750,764 S | 3/2016 | DeSocio |
| 9,332,995 B2 | 5/2016 | Russo |
| 9,526,763 B2 | 12/2016 | Rohloff et al. |
| 9,539,200 B2 | 1/2017 | Lautenbach |
| 9,572,889 B2 | 2/2017 | Alessi et al. |
| D789,539 S | 6/2017 | Kleiner et al. |
| D789,540 S | 6/2017 | Gyorgy |
| 9,682,127 B2 | 6/2017 | Alessi et al. |
| RE46,577 E | 10/2017 | Collins et al. |
| 9,889,085 B1 | 2/2018 | Alessi et al. |
| 2001/0012511 A1 | 8/2001 | Bezwada et al. |
| 2001/0021377 A1 | 9/2001 | Jamiolkowski et al. |
| 2001/0021822 A1 | 9/2001 | Ayer |
| 2001/0022974 A1 | 9/2001 | Ayer |
| 2001/0026793 A1 | 10/2001 | Jamiolkowski et al. |
| 2001/0027311 A1 | 10/2001 | Chen et al. |
| 2001/0031790 A1 | 10/2001 | Beisswenger |
| 2001/0036472 A1 | 11/2001 | Wong et al. |
| 2001/0040326 A1 | 11/2001 | Balczun |
| 2002/0001631 A1 | 1/2002 | Okumu |
| 2002/0004481 A1 | 1/2002 | Cleland et al. |
| 2002/0012818 A1 | 1/2002 | Ruppi et al. |
| 2002/0034532 A1 | 3/2002 | Brodbeck et al. |
| 2002/0037309 A1 | 3/2002 | Jaworowicz et al. |
| 2002/0048600 A1 | 4/2002 | Bhatt et al. |
| 2002/0098180 A1 | 7/2002 | Lei |
| 2002/0136848 A1 | 9/2002 | Yoshii et al. |
| 2002/0137666 A1 | 9/2002 | Beeley et al. |
| 2002/0141985 A1 | 10/2002 | Pittner et al. |
| 2002/0197185 A1 | 12/2002 | Jamiolkowski et al. |
| 2002/0197235 A1 | 12/2002 | Moran |
| 2003/0032947 A1 | 2/2003 | Harper et al. |
| 2003/0044467 A1 | 3/2003 | Brodbeck et al. |
| 2003/0045454 A1 | 3/2003 | Okumu et al. |
| 2003/0059376 A1 | 3/2003 | Libbey et al. |
| 2003/0060425 A1 | 3/2003 | Ahlem et al. |
| 2003/0097121 A1 | 5/2003 | Jolly et al. |
| 2003/0104063 A1 | 6/2003 | Babcock et al. |
| 2003/0108608 A1 | 6/2003 | Laridon et al. |
| 2003/0108609 A1 | 6/2003 | Berry et al. |
| 2003/0113380 A1 | 6/2003 | Ramstack et al. |
| 2003/0114837 A1 | 6/2003 | Peterson et al. |
| 2003/0118660 A1 | 6/2003 | Rickey et al. |
| 2003/0138403 A1 | 7/2003 | Drustrup |
| 2003/0138491 A1 | 7/2003 | Tracy et al. |
| 2003/0157178 A1 | 8/2003 | Chen et al. |
| 2003/0170289 A1 | 9/2003 | Chen et al. |
| 2003/0180364 A1 | 9/2003 | Chen et al. |
| 2003/0186858 A1 | 10/2003 | Arentsen |
| 2003/0191099 A1 | 10/2003 | Bohlmann et al. |
| 2003/0211974 A1 | 11/2003 | Brodbeck et al. |
| 2003/0215515 A1 | 11/2003 | Truong-Le et al. |
| 2004/0001689 A1 | 1/2004 | Goldsmith et al. |
| 2004/0001889 A1 | 1/2004 | Chen et al. |
| 2004/0002442 A1 | 1/2004 | Pan et al. |
| 2004/0022859 A1 | 2/2004 | Chen et al. |
| 2004/0024068 A1 | 2/2004 | Levy et al. |
| 2004/0024069 A1 | 2/2004 | Chen et al. |
| 2004/0029784 A1 | 2/2004 | Hathaway |
| 2004/0039376 A1 | 2/2004 | Peery et al. |
| 2004/0097906 A1 | 5/2004 | Fereira et al. |
| 2004/0101557 A1 | 5/2004 | Gibson et al. |
| 2004/0102762 A1 | 5/2004 | Gilbert |
| 2004/0115236 A1 | 6/2004 | Chan et al. |
| 2004/0142867 A1 | 7/2004 | Oi et al. |
| 2004/0142902 A1 | 7/2004 | Struijker-Boudier |
| 2004/0151753 A1 | 8/2004 | Chen et al. |
| 2004/0157951 A1 | 8/2004 | Wolf |
| 2004/0198654 A1 | 10/2004 | Glaesner et al. |
| 2004/0209801 A1 | 10/2004 | Brand et al. |
| 2004/0224903 A1 | 11/2004 | Berry et al. |
| 2004/0225113 A1 | 11/2004 | LaFleur et al. |
| 2004/0243106 A1 | 12/2004 | Ayer |
| 2004/0265273 A1 | 12/2004 | Li et al. |
| 2004/0266683 A1 | 12/2004 | Hathaway et al. |
| 2004/0266692 A1 | 12/2004 | Young et al. |
| 2005/0004557 A1 | 1/2005 | Russell |
| 2005/0008661 A1 | 1/2005 | Fereira et al. |
| 2005/0009742 A1 | 1/2005 | Bertilsson et al. |
| 2005/0010196 A1 | 1/2005 | Fereira et al. |
| 2005/0010942 A1 | 1/2005 | Kim et al. |
| 2005/0070883 A1 | 3/2005 | Brown et al. |
| 2005/0070927 A1 | 3/2005 | Feinberg |
| 2005/0079200 A1 | 4/2005 | Rathenow et al. |

(56) References Cited

U.S. PATENT DOCUMENTS

| | | |
|---|---|---|
| 2005/0079202 A1 | 4/2005 | Chen et al. |
| 2005/0095284 A1 | 5/2005 | Trautman |
| 2005/0101943 A1 | 5/2005 | Ayer et al. |
| 2005/0106214 A1 | 5/2005 | Chen |
| 2005/0112188 A1 | 5/2005 | Eliaz et al. |
| 2005/0118206 A1 | 6/2005 | Luk et al. |
| 2005/0118221 A1 | 6/2005 | Blakely et al. |
| 2005/0131386 A1 | 6/2005 | Freeman et al. |
| 2005/0131389 A1 | 6/2005 | Peterson et al. |
| 2005/0175701 A1 | 8/2005 | Pan et al. |
| 2005/0201980 A1 | 9/2005 | Moran |
| 2005/0215475 A1 | 9/2005 | Ong et al. |
| 2005/0216087 A1 | 9/2005 | Zucherman, Jr. et al. |
| 2005/0266087 A1 | 12/2005 | Junnarkar et al. |
| 2005/0271702 A1 | 12/2005 | Wright et al. |
| 2005/0276856 A1 | 12/2005 | Fereira et al. |
| 2005/0281879 A1 | 12/2005 | Chen et al. |
| 2006/0013879 A9 | 1/2006 | Brodbeck et al. |
| 2006/0014678 A1 | 1/2006 | Cowley et al. |
| 2006/0030526 A1 | 2/2006 | Liu et al. |
| 2006/0069029 A1 | 3/2006 | Kolterman et al. |
| 2006/0073182 A1 | 4/2006 | Wong et al. |
| 2006/0084604 A1 | 4/2006 | Kitaura et al. |
| 2006/0084922 A1 | 4/2006 | Botha |
| 2006/0094652 A1 | 5/2006 | Levy et al. |
| 2006/0094693 A1 | 5/2006 | Aziz et al. |
| 2006/0106399 A1 | 5/2006 | Taras et al. |
| 2006/0141040 A1 | 6/2006 | Chen et al. |
| 2006/0142234 A1 | 6/2006 | Chen et al. |
| 2006/0160736 A1 | 7/2006 | Nadler |
| 2006/0178304 A1 | 8/2006 | Juul-Mortensen et al. |
| 2006/0193918 A1 | 8/2006 | Rohloff et al. |
| 2006/0216242 A1 | 9/2006 | Rohloff et al. |
| 2006/0224145 A1 | 10/2006 | Gills |
| 2006/0233841 A1 | 10/2006 | Brodbeck et al. |
| 2006/0246138 A1 | 11/2006 | Rohloff et al. |
| 2006/0251618 A1 | 11/2006 | Dennis et al. |
| 2006/0263433 A1 | 11/2006 | Ayer et al. |
| 2006/0264890 A1 | 11/2006 | Moberg et al. |
| 2006/0280795 A1 | 12/2006 | Penhasi et al. |
| 2006/0293232 A1 | 12/2006 | Levy et al. |
| 2007/0027105 A1 | 2/2007 | Junnarkar et al. |
| 2007/0149011 A1 | 6/2007 | Kent et al. |
| 2007/0166352 A1 | 7/2007 | Wright et al. |
| 2007/0248572 A1 | 10/2007 | Moran et al. |
| 2007/0281024 A1 | 12/2007 | Lautenbach et al. |
| 2008/0020016 A1 | 1/2008 | Li et al. |
| 2008/0038316 A1 | 2/2008 | Wong et al. |
| 2008/0064636 A1 | 3/2008 | Bloom et al. |
| 2008/0065090 A1 | 3/2008 | Scribner et al. |
| 2008/0091176 A1 | 4/2008 | Alessi et al. |
| 2008/0110515 A1 | 5/2008 | Angelosanto et al. |
| 2008/0112994 A1 | 5/2008 | Junnarkar et al. |
| 2008/0200383 A1 | 8/2008 | Jennings et al. |
| 2008/0207512 A1 | 8/2008 | Roth et al. |
| 2008/0208194 A1 | 8/2008 | Bickenbach |
| 2008/0226625 A1 | 9/2008 | Berry et al. |
| 2008/0226689 A1 | 9/2008 | Berry et al. |
| 2008/0260838 A1 | 10/2008 | Hokenson et al. |
| 2008/0260840 A1 | 10/2008 | Alessi et al. |
| 2008/0269725 A1 | 10/2008 | Deem et al. |
| 2008/0312157 A1 | 12/2008 | Levy et al. |
| 2009/0022727 A1 | 1/2009 | Houston et al. |
| 2009/0036364 A1 | 2/2009 | Levy et al. |
| 2009/0042781 A1 | 2/2009 | Petersen et al. |
| 2009/0074734 A1 | 3/2009 | Rottiers |
| 2009/0087408 A1 | 4/2009 | Berry et al. |
| 2009/0156474 A1 | 6/2009 | Roth et al. |
| 2009/0163447 A1 | 6/2009 | Maggio |
| 2009/0186817 A1 | 7/2009 | Ghosh et al. |
| 2009/0202481 A1 | 8/2009 | Li et al. |
| 2009/0202608 A1 | 8/2009 | Alessi et al. |
| 2009/0209460 A1 | 8/2009 | Young et al. |
| 2009/0210019 A1 | 8/2009 | Kim et al. |
| 2009/0215694 A1 | 8/2009 | Kolterman et al. |
| 2009/0234392 A1 | 9/2009 | Dziedzic |
| 2009/0247463 A1 | 10/2009 | Wright et al. |
| 2009/0254143 A1 | 10/2009 | Tweden et al. |
| 2009/0286723 A1 | 11/2009 | Levy et al. |
| 2009/0312246 A1 | 12/2009 | Baron et al. |
| 2010/0092566 A1 | 4/2010 | Alessi et al. |
| 2010/0105627 A1 | 4/2010 | Salama et al. |
| 2010/0144621 A1 | 6/2010 | Kim et al. |
| 2010/0185184 A1 | 7/2010 | Alessi et al. |
| 2010/0297209 A1 | 11/2010 | Rohloff et al. |
| 2010/0298840 A1 | 11/2010 | Schwartz |
| 2011/0076317 A1 | 3/2011 | Alessi et al. |
| 2011/0091527 A1 | 4/2011 | Moonen et al. |
| 2011/0104111 A1 | 5/2011 | Rohloff et al. |
| 2011/0152181 A1 | 6/2011 | Alsina-Fernandez et al. |
| 2011/0152182 A1 | 6/2011 | Alsina-Fernandez et al. |
| 2011/0160708 A1 | 6/2011 | Berry et al. |
| 2011/0166554 A1 | 7/2011 | Alessi et al. |
| 2011/0264077 A1 | 10/2011 | Rohloff et al. |
| 2011/0306549 A1 | 12/2011 | Tatarkiewicz et al. |
| 2012/0208755 A1 | 8/2012 | Leung |
| 2013/0030417 A1 | 1/2013 | Alessi |
| 2013/0034210 A1 | 2/2013 | Rohloff et al. |
| 2013/0052237 A1 | 2/2013 | Eliaz et al. |
| 2014/0058425 A1 | 2/2014 | Porat |
| 2014/0121741 A1 | 5/2014 | Bennett et al. |
| 2014/0257272 A1 | 9/2014 | Clark, III et al. |
| 2014/0378900 A1 | 12/2014 | Alessi et al. |
| 2015/0111818 A1 | 1/2015 | Alessi et al. |
| 2015/0057227 A1 | 2/2015 | Leung |
| 2015/0133791 A1 | 5/2015 | Sato et al. |
| 2015/0231062 A1 | 8/2015 | Lautenbach et al. |
| 2015/0231256 A1 | 8/2015 | Berry et al. |
| 2015/0297509 A1 | 10/2015 | Schwarz |
| 2016/0022582 A1 | 1/2016 | Alessi et al. |
| 2016/0030337 A1 | 2/2016 | Kuzma et al. |
| 2016/0354115 A1 | 12/2016 | Smith et al. |
| 2016/0354305 A1 | 12/2016 | Alessi et al. |
| 2017/0056476 A1 | 3/2017 | Rohloff et al. |
| 2017/0079906 A1 | 3/2017 | Alessi et al. |
| 2017/0119854 A1 | 5/2017 | Alessi et al. |
| 2017/0119855 A1 | 5/2017 | Berry et al. |
| 2017/0181964 A1 | 6/2017 | Lautenbach et al. |
| 2017/0252409 A1 | 9/2017 | Leung |
| 2017/0273706 A1 | 9/2017 | Mirza et al. |
| 2017/0319470 A1 | 11/2017 | Eliaz et al. |
| 2017/0319662 A1 | 11/2017 | Berry et al. |
| 2017/0348392 A1 | 12/2017 | Rohloff et al. |
| 2017/0368145 A1 | 12/2017 | Alessi et al. |
| 2018/0009871 A1 | 1/2018 | Blackwell et al. |

FOREIGN PATENT DOCUMENTS

| | | |
|---|---|---|
| EP | 0254394 | 1/1988 |
| EP | 0295411 | 12/1988 |
| EP | 0302582 A1 | 2/1989 |
| EP | 0368339 | 5/1990 |
| EP | 0373867 | 6/1990 |
| EP | 0431942 | 6/1991 |
| EP | 0486959 A1 | 5/1992 |
| EP | 0521586 A1 | 1/1993 |
| EP | 0596161 | 5/1994 |
| EP | 0379147 | 9/1994 |
| EP | 0627231 | 12/1994 |
| EP | 0729747 | 5/1997 |
| EP | 0771817 | 5/1997 |
| EP | 0841359 | 5/1998 |
| EP | 0767689 | 6/1999 |
| EP | 1046399 | 10/2000 |
| EP | 1084703 | 3/2001 |
| EP | 1300129 A2 | 4/2003 |
| EP | 1300173 A2 | 4/2003 |
| EP | 1600187 | 1/2009 |
| EP | 2133073 A1 | 12/2009 |
| EP | 2020990 | 9/2010 |
| FR | 640907 | 7/1928 |
| GB | 1049104 | 11/1966 |
| GB | 1518683 | 7/1978 |
| GB | 2501400 | 10/2013 |

(56) References Cited

FOREIGN PATENT DOCUMENTS

| | | |
|---|---|---|
| JP | H02124814 A | 5/1990 |
| JP | H07196479 A | 8/1995 |
| JP | 9241153 | 9/1997 |
| JP | 11-100353 | 4/1999 |
| JP | 2006/213727 A | 8/2006 |
| NL | 9100160 | 4/1994 |
| NZ | 592113 | 8/2012 |
| TW | 200634060 | 10/2006 |
| WO | WO1989003678 A1 | 5/1989 |
| WO | WO1990013285 A1 | 11/1990 |
| WO | WO1990013361 A1 | 11/1990 |
| WO | WO1990013780 A1 | 11/1990 |
| WO | WO 91/07160 | 5/1991 |
| WO | WO1992019241 A1 | 11/1992 |
| WO | WO 93/06819 | 4/1993 |
| WO | WO 93/06821 | 4/1993 |
| WO | WO 93/008832 | 5/1993 |
| WO | WO 93/09763 | 5/1993 |
| WO | WO 93/23083 | 11/1993 |
| WO | WO 94/09743 | 5/1994 |
| WO | WO1994010982 A1 | 5/1994 |
| WO | WO 94/21262 | 9/1994 |
| WO | WO 95/01167 | 1/1995 |
| WO | WO 95/09006 | 4/1995 |
| WO | WO 95/09007 | 4/1995 |
| WO | WO1995013799 A1 | 5/1995 |
| WO | WO 95/34285 | 12/1995 |
| WO | WO 96/001134 | 1/1996 |
| WO | WO 96/003116 | 2/1996 |
| WO | WO1996036317 A1 | 11/1996 |
| WO | WO 96/39142 | 12/1996 |
| WO | WO 96/40049 | 12/1996 |
| WO | WO 96/40139 | 12/1996 |
| WO | WO 96/40355 | 12/1996 |
| WO | WO 97/15289 | 5/1997 |
| WO | WO 97/15296 | 5/1997 |
| WO | WO 97/28181 | 8/1997 |
| WO | WO1997031943 A1 | 9/1997 |
| WO | WO1997044039 A1 | 11/1997 |
| WO | WO 97/46204 | 12/1997 |
| WO | WO 97/47339 | 12/1997 |
| WO | WO 98/00152 | 1/1998 |
| WO | WO 98/00157 | 1/1998 |
| WO | WO 98/00158 | 1/1998 |
| WO | WO 98/02169 | 1/1998 |
| WO | WO1997041837 A3 | 2/1998 |
| WO | WO1998007412 A1 | 2/1998 |
| WO | WO 98/16250 | 4/1998 |
| WO | WO 98/17315 | 4/1998 |
| WO | WO 98/20930 | 5/1998 |
| WO | WO 98/27960 | 7/1998 |
| WO | WO 98/027962 | 7/1998 |
| WO | WO 98/27963 | 7/1998 |
| WO | WO 98/030231 | 7/1998 |
| WO | WO 98/32463 | 7/1998 |
| WO | WO1998030231 A1 | 7/1998 |
| WO | WO 98/42317 | 10/1998 |
| WO | WO 98/47487 | 10/1998 |
| WO | WO 98/51282 | 11/1998 |
| WO | WO 99/03453 | 1/1999 |
| WO | WO 99/04767 | 2/1999 |
| WO | WO 99/004768 | 2/1999 |
| WO | WO1999012549 A2 | 3/1999 |
| WO | WO 99/16419 | 4/1999 |
| WO | WO 99/025728 | 5/1999 |
| WO | WO 99/29306 | 6/1999 |
| WO | WO 99/033446 | 7/1999 |
| WO | WO 99/33449 | 7/1999 |
| WO | WO 99/39700 | 8/1999 |
| WO | WO 99/040788 | 8/1999 |
| WO | WO 99/044659 | 9/1999 |
| WO | WO 99/062501 | 12/1999 |
| WO | WO 99/064061 | 12/1999 |
| WO | WO 00/013663 | 3/2000 |
| WO | WO 00/029206 | 5/2000 |
| WO | WO 00/038652 | 7/2000 |
| WO | WO 00/039280 | 7/2000 |
| WO | WO 00/040273 | 7/2000 |
| WO | WO 00/041548 | 7/2000 |
| WO | WO 00/045790 | 8/2000 |
| WO | WO 00/054745 | 9/2000 |
| WO | WO2000059476 A1 | 10/2000 |
| WO | WO 00/066138 | 11/2000 |
| WO | WO 00/067728 | 11/2000 |
| WO | WO2000066087 A2 | 11/2000 |
| WO | WO2001019345 A1 | 3/2001 |
| WO | WO2001028525 A2 | 4/2001 |
| WO | WO 01/043528 | 6/2001 |
| WO | WO 01/051041 | 7/2001 |
| WO | WO 01/78683 | 10/2001 |
| WO | WO 02/028366 | 4/2002 |
| WO | WO 02/036072 | 5/2002 |
| WO | WO 02/043800 | 6/2002 |
| WO | WO 02/045752 | 6/2002 |
| WO | WO 02/47716 | 6/2002 |
| WO | WO 02/067895 | 9/2002 |
| WO | WO 02/069983 | 9/2002 |
| WO | WO 02/76344 | 10/2002 |
| WO | WO 02/085428 | 10/2002 |
| WO | WO 03/000230 | 1/2003 |
| WO | WO 03/007981 | 1/2003 |
| WO | WO 03/011892 | 2/2003 |
| WO | WO 03/024357 | 3/2003 |
| WO | WO 03/024503 | 3/2003 |
| WO | WO2003020245 A1 | 3/2003 |
| WO | WO 03/030923 | 4/2003 |
| WO | WO 03/041684 | 5/2003 |
| WO | WO 03/041757 | 5/2003 |
| WO | WO 03/053400 | 7/2003 |
| WO | WO2003066585 A2 | 8/2003 |
| WO | WO 03/072113 | 9/2003 |
| WO | WO 03/072133 | 9/2003 |
| WO | WO 04/002565 | 1/2004 |
| WO | WO2004034975 A2 | 4/2004 |
| WO | WO2004035754 A2 | 4/2004 |
| WO | WO2004035762 A2 | 4/2004 |
| WO | WO2004036186 A2 | 4/2004 |
| WO | WO 04/052336 | 6/2004 |
| WO | WO 04/056338 | 7/2004 |
| WO | WO 04/089335 | 10/2004 |
| WO | WO2004103342 A2 | 12/2004 |
| WO | WO 05/048930 | 6/2005 |
| WO | WO 05/048952 | 6/2005 |
| WO | WO 05/102293 | 11/2005 |
| WO | WO2005102293 A1 | 11/2005 |
| WO | WO2005110425 | 11/2005 |
| WO | WO 06/017772 | 2/2006 |
| WO | WO 06/023526 | 3/2006 |
| WO | WO 06/081279 | 8/2006 |
| WO | WO 06/083761 | 8/2006 |
| WO | WO 06/084139 | 8/2006 |
| WO | WO 06/086727 | 8/2006 |
| WO | WO 06/101815 | 9/2006 |
| WO | WO 06/111169 | 10/2006 |
| WO | WO2006/131730 | 12/2006 |
| WO | WO 07/024700 | 3/2007 |
| WO | WO 07/056681 | 5/2007 |
| WO | WO 07/075534 | 7/2007 |
| WO | WO 07/084460 | 7/2007 |
| WO | WO 07/133778 | 11/2007 |
| WO | WO 07/140416 | 12/2007 |
| WO | WO 08/021133 | 2/2008 |
| WO | WO2008/041245 A2 | 4/2008 |
| WO | WO 08/061355 | 5/2008 |
| WO | WO2008/086086 A2 | 7/2008 |
| WO | WO 08/133908 | 11/2008 |
| WO | WO 08/134425 | 11/2008 |
| WO | WO 09/109927 | 9/2009 |
| WO | WO2009143285 A2 | 11/2009 |
| WO | WO 2011/037623 A1 | 3/2011 |

(56) References Cited

FOREIGN PATENT DOCUMENTS

| WO | WO 2011/138421 A1 | 11/2011 |
|---|---|---|
| WO | WO 2013/004983 A1 | 1/2013 |

OTHER PUBLICATIONS

Yu et al., "Glucagon-like peptide 1 based therapy for type 2 diabetes", World Journal of Pediatrics vol. 4, No. 1, Feb. 1, 2008, pp. 8-13.
Taylor et al., "Day-long subcutaneous infusion of exenatide lowers glycemia in patients with type 2 diabetes", Horm Metab Res 37: 627-632 (2005).
Gao et al., "Target-Mediated Pharmacokinetic and Pharmacodynamic Model of Exendin-4 in Rats, Monkeys. and Humans," Drug Metabolism and Disposition, vol. 40, No. 5, pp. 990-997 (2012).
Adolf, "Human interferon omega—a review," Mult. Sclr. 1:S44-47 (1995).
Costantino et al., "Protein Spray Freeze Drying. 2. Effect of Formulation Variables on particle Size and Stability," J. Pharm. Sci. 91:388-395 (2002).
Henry et al., "Comparing ITCA 650, continuous subcutaneous delivery of exenatide via DUROS® device, vs. twice daily exenatide injections in metformin-treated type 2 diabetes," oral presentation at the 46th Annual Meeting of the European Association for the Study of Diabetes in Stockholm, Sweden , 21 pages (Sep. 20-24, 2010).
Huggins et al., "Synergistic antiviral effects of ribavirin and the C-nucleoside analogs tiazofurin and selenazofurin against togaviruses, bunyaviruses, and arenaviruses," Antimicrobial Agents & Chemotherapy, 26(4):476-480 (1984).
Ishiwata et al., "Clinical effects of the recombinant feline interferon-omega on experimental parvovirus infection in beagle dogs," J. Vet. Med. Sci. 60(8):911-917 (1998).
Johnson et al., "How interferons fight disease," Sci. Am. 270(5):68-75 (May 1994).
Lublin et al., "Defining the clinical course of multiple sclerosis: results of an international survey," Neurology. 46:907-911 (1996).
Madsbad, "Exenatide and liraglutide: different approaches to develop GLP-1 receptor agonists (incretin mimetics)—preclinical and clinical results," Best Practice & Research Clinical Endocrinology & Metabolism 23:463-77 (2009).
Nielsen, "Incretin mimetics and DPP-IV inhibitors for the treatment of type 2 diabetes," Drug Discovery Today 10(10):703-710 (May 15, 2005).
Palmeri et al., "5-Fluorouracil and recombinant α-interferon-2a in the treatment of advanced colorectal carcinoma: a dose optimization study," J. Chemotherapy 2(5):327-330 (Oct. 1990).
Patti et al., "Natural interferon-b treatment of relapsing-remitting and secondary-progressive multiple sclerosis patients: two-year study," Acta. Neurol. Scand. 100:283-289 (1999).
Paty et al., "Interferon beta-1 b is effective in relapsing-remitting multiple sclerosis," Neurology 43:662-667 (1993).
PCT International Search Report for PCT/US2009/00+D15360916, 4 pages (dated Aug. 12, 2009).
"Intarcia Therapeutics Announces Final Results from a Phase 2 Study of Injectable Omega Interferon plus Ribavirin for the Treatment of Hepatitis C Genotype-1," NLV Partners Press Coverage Portfolio News (Apr. 12, 2007) (Press Release).
Quianzon et al., "Lixisenatide-Once-daily Glucagon-like Peptide-1 Diabetes," US Endocrinology 7(2):104-109 (2011).
Ratner et al., "Dose-dependent effects of the one-daily GLP-1 receptor agonist lixisenatide in patients with Type 2 diabetes inadequately controlled with metfmmin: a randomized, double-blind, placebo-controlled trial," Diabetic Medicine 27(9):1024-1032 (Sep. 2010).
Roberts et al., "The Evolution of the Type I Interferons1," J. Interferon Cytokine Res. 18(10):805-816 (Oct. 1998).
Rohloff et al., "DUROS Technology Delivers Peptides and Proteins at Consistent Rate Continuously for 3 to 12 Months," J. Diabetes Sci. & Tech., 2(3):461-467 (May 1, 2008).

"Sequence Listings for International Patent Application Publication No. W02009109927, WIPO Patentscope", http://patentscope.wipo.int/search/docservicepdf_pct/id00000008776887, 1 page (last visited Nov. 14, 2012).
Shire et al., "Challenges in the Development of High Protein Concentration Formulations," J. Pharm. Sci. 93:1390-1402 (2004).
Smith, "Peripheral Neuro-hormones as a Strategy to Treat Obesity," oral presentation at the 2007 Cardiometabolic Health Congress in Boston, MA, pp. 1-35 (Sep. 26-29, 2007).
Written Opinion for International Patent Application No. PCT/US2009/005629 (corresponding to U.S. Appl. No. 12/587,946), 5 pages (dated Apr. 15, 2011).
Zhang et al., "Efficacy observations of different dosages of interferon to treat 150 Hepatitis B carriers," Current Physician 2(12):45-46 (1997).
Pratley et al., "Targeting Incretins in Type 2 Diabetes: Role of GLP-1 Receptor Agonists and DPP-4 Inhibitors," Rev. Diabet. Stud., 5(2):73-94 (2008).
Gonzalez, et al., "Hemoglobin A1c: A Reliable and Accurate Test for Diabetes Care? A Prospective Study in Mexico," Salud Publica Mex 55:462-468 (2013).
Ahn et al., "A New Approach to Search for the Bioactive Confirmation of Glucagon: Positional Cyclization Scanning" Journal of Medicinal Chemistry, vol. 44, No. 19, (2001): 3109-3116.
Glumetza Brochure 2009, 13 Pages.
Erowid,"Introduction to the Federal Controlled Substance Analog Act" 2001.
Li et al. ("Glucagon-Like Peptide-I Receptor Agonists Versus Insulin Glargine for Type 2 Diabetes Mellitus: A Systematic Review and Meta-Analysis of Randomized Controlled Trials" in Current Therapeutic Research, vol. 71, No. 4, Aug. 2010.
"Abstracts 2007," Diabetologia Clinical & Experimental Diabetes & Metabolism, Springer, Berlin, Germany, vol. 50 S243 (Aug. 21, 2007) (paragraph [0586]) (XP002538652).
Jetschmann et al., "Open-label rising-dose study of omega interferon in IFN-naive patients with chronic hepatitis C," Gastroenterology 122:A278-A347 (Apr. 1, 2002) (Abstract M1454).
Bray, "Gut Signals and Energy Balance: Ghrelin, Peptide YY, Leptin, and Amylin," (Dec. 19, 2007) (slides and transcript for presentation at Medscape CME).
"Implantable infusion pumps: technology poised for takeoff," BBI Newsletter 17(12):209-211 (Dec. 1994).
Adamson et al., "Phase I trial and pharmacokinetic study of all-trans-retinoic acid administered on an intermittent schedule in combination with interferon-alpha2a in pediatric patients with refractory cancer," J. Clin. Oncol. 15(11):3330-3337 (Nov. 1997).
Adolf et al., "Monoclonal antibodies and enzyme immunoassays specific for human interferon (IFN) ω1: evidence that IFN-ω1 is a component of human leukocyte IFN," Virology 175(2):410-471 (Apr. 1990).
Adolf et al., "Antigenic structure of human interferon ω1 (Interferon αII1): comparison with other human interferons," J. Gen. Virol. 68(6):1669-1676 (Jun. 1987).
Adolf et al., "Purification and characterization of natural human interferon ω1," J. Bio. Chem. 265(16):9290-9295 (Jun. 1990).
Adolf et al., "Human interferon ω1: isolation of the gene, expression in Chinese hamster ovary cells and characterization of the recombinant protein," Biochim. Biophys. Acta 108(9):167-174 (Jun. 1991).
ANDRX Pharmaceuticals, LLC, ANDA for Concerta® Extended-Release Tablets, 6 pages (correspondence dated Sep. 6, 2005).
ASTM International, Annual Book of ASTM Standards, 8.02:208-211, 584-587 (1984).
Ansel et al., "Dosage Form Design: Pharmaceutical and Formulation Considerations," Pharmaceutical Dosage Forms and Drug Delivery Systems, Ch. 3 at 87-92 (7th ed. Lippincott Williams & Wilkins 1999).
Ansel et al., "Modified-Release Dosage Forms and Drug Delivery Systems," Pharmaceutical Dosage Forms and Drug Delivery Systems, Ch. 8 at 229-243 (7th ed. Lippincott Williams & Wilkins 1999).
Aulitzky, "Successful Treatment of Metastatic Renal Cell Carcinoma With a Biologically Active Dose of Recombinant Interferon-Gama," Journal of Clinical Oncology 7(12):1875-1884 (1989).

(56) References Cited

OTHER PUBLICATIONS

Hauck, "Engineer's Guide to Plastics," Materials Engineering 5(72):38-45 (Jul. 17, 1972).
Bailon et al., "Rational Design of a Potent, Long-lasting Form of Interferon: A 40 kDa Branched Polyethylene Glycol-conjugated Interferon Alpha-2a for the Treatment of Hepatitis C," Bioconjugate Chemistry 12(2):195-202 (2001).
Bakan et al., "Physicochemical Characterization of a Synthetic Lipid Emulsion for Hepatocyte-Selective Delivery of Lipophilic Compounds: Application to Polyiodinated triglycerides as Contrast Agents for Computed Tomography," J. Pharm. Sci., 85(9):908-914 (1996).
Bakhtiar et al, "Taking Delivery," Soap Perfumery & Cosmetics 76(3):59-65 (2003) (liposomes in cosmetic delivery systems).
Balkwill,F., "Interferons," Lancet 1(8646):1060-1063 (May 1989).
Bauer et al., "Non-aqueous emulsions as vehicles for capsule fillings," Drug Dev. & Industrial Pharmacy 10(5):699-712 (1984).
Bekkering et al., "Estimation of early hepatitis C viral clearance in patients receiving daily interferon and ribavirin therapy using a mathematical model," Hepatology 33(2):419-423 (Feb. 2001).
Bell et al., "Hamster preproglucagon contains the sequence of glucagon and two related peptides," Nature 302:716-718 (1983).
Bell et al, "Impact of moisture on thermally induced denaturation and decomposition of lyophilized bovine somatotropin," Drug Delivery Research & Dev. Biopolymers, (35):201-209 (1995).
Bertoncello et al., "Haematopoietic radioprotection by Cremophor EL: a polyethoxylated castor oil," Int. J. Radiat. Biol. 67(1):57-64 (1995).
Bohlinder et al., "Use and characteristics of a novel lipid particle-forming matrix as a drug-carrier system," Euro. J. Pharm. Sci. 2(4):271-279 (1994).
Bolinger et al., "Recombinant interferon γ for treatment of chronic granulomatous disease and other disorders," Clin. Pharm. 11(10):834-850 (Oct. 1992).
Bonkovsky et al., "Outcomes research in chronic viral hepatitis C: effects of interferon therapy," Can. J. Gastroenterol. 14(Supp. B):21B-29B (Jul.-Aug. 2000).
Borden et al., "Second-generation interferons for cancer: clinical targets," Semin. Cancer Biol. 10(2):125-144 (Apr. 2000).
Boué et al., "Antiviral and antiluteolytic activity of recombinant bovine IFN-ω1 obtained from Pichia pastoris," J. Interferon & Cytokine Res. 20:677-683 (2000).
Buckwold et. al. "Antiviral activity of CHO-SS cell-derived human omega interferon and other human interferons against HCV RNA replicons and related viruses," Antiviral Res. 73(2):118-25 (Feb. 2007) (Epub Sep. 11, 2006).
Cantor, "Theory of lipid monolayers comprised of mixtures of flexible and stiff amphiphiles in anthermal solvents: fluid phase coexistence," J. Chem. Physics 104(20):8082-8095 (1996).
CAS No. 56-81-5 (Nov. 16, 1984).
Chang et al., "Biodegradable polyester implants and suspension injection for sustained release of a cognitive enhancer," Pharm. Tech. 20(1):80-84 (1996).
Chapman et al., "Physical Studies of Phospholipids. VI. Thermotropic and Lyotropic Mesomorphism of Some 1,2-Diacylphosphatidylcholines (lecithins)," Chem. & Physics of Lipids 1(5):445-475 (1967).
Chaumeil, "Micronization: a method of improving the bioavailability of poorly soluble drugs," Methods & Findings in Experimental & Clinical Pharmacology 20(3):211-215 (1998).
Clark et al., "The diabetic Zucker fatty rat," Proc. Soc. Exp. Biol. 173(1):68-75 (1983).
Condino-Neto, "Interferon-γ improves splicing efficiency of CYBB gene transcripts in an interferon responsive variant of chronic granulomatous disease due to a splice site consensus region mutation," Blood 95(11):3548-3554 (Jun. 2000).
Darney, "Subdermal progestin implant contraception," Current Opinion in Obstetrics & Gynecology 3:470-476 (1991).
Das et al., "Reviewing Antisense Oligonucleotide Therapy: Part 2, Delivery Issues," BioPharm, 2(11):44-51 (1999).

Dash et al., "Therapeutic applications of implantable drug delivery systems," Journal of Pharmacological and Toxicological Methods, 40(1):1-12 (1998).
Davis et al., "Durability of viral response to interferon alone or in combination with oral ribavirin in patients with chronic hepatitis C," Prog. Abstr. 50th Annu. Mtg. Postgrad. Courses Am. Assn. Study Liver Dis., Dallas, TX (Nov. 5-9, 1999)(Abstract 570 ).
Deacon et al., "GLP-1-(9-36) amide reduces blood glucose in anesthetized pigs by a mechanism that does not involve insulin secretion," Am. J. Physiol. Endocrinol. Metab., 282:E873-E879 (2002).
Desai et al., "Protein structure in the lyophilized state: a hydrogen isotope exchange/NMR study with bovine pancreatic trypsin inhibitor," J. Am. Chem. Soc. 116(21):9420-9422 (1994).
Di Marco et al., "Combined treatment of relapse of chronic hepatitis C with high-dose α-2B interferon plus ribavirin for 6 or 12 months," Prog. Abstr. 50th Annu. Mtg. Postgrad. Courses Am. Assn. Study Liver Dis., Dallas, TX (Nov. 5-9, 1999)(Abstract 569).
Dorr et al., "Phase I-II trial of interferon-alpha 2b by continuous subcutaneous infusion over 28 days," J. Interferon Res. 8:717-725 (1988).
Uhlig et al., "The electro-osmotic actuation of implantable insulin micropumps," J. Biomed. Materials Res. 17:931-943 (1983).
Efendic et al., "Overview of incretin hormones," Horm. Metab. Res., 36(11-12):742-746 (2004).
Eissele et al., "Rat gastric somatostatin and gastrin release: interactions of exendin-4 and truncated glucagon-like peptide-1 (GLP-1) amide," Life Sci., 55(8):629-634 (1994).
Elias et al., "Infusional Interleukin-2 and 5-fluorouracil with subcutaneous interferon-α for the treatment of patients with advanced renal cell carcinoma: a southwest oncology group Phase II study," Cancer 89(3):597-603 (Aug. 2000).
Eng et al., "Isolation and characterization of exendin-4, an exendin-3 analogue, from Heloderma suspectum venom. Further evidence for an exendin receptor on dispersed acini from guinea pig pancreas," J. Biol. Chem., 267(11):7402-7405 (1992).
Eng et al., "Purification and structure of exendin-3, a new pancreatic secretagogue isolated from Heloderma horridum venom," J. Biol. Chem., 265(33):20259-20262 (1990).
Eppstein et al., "Biological activity of liposome-encapsulated murine interferon γ is mediated by a cell membrane receptor," PNAS USA 82:3688-3692 (1985).
Eros et al., "Multiple phase emulsions as controlled drug delivery therapeutic systems," Proc.-Conf. Colloid Chem. 193-196 (1993).
Fang et al., "The impact of baseline liver histology on virologic response to interferon α-2b±ρ ribavirin therapy in patients with chronic hepatitis C," Prog. Abstr. 50th Annu. Mtg. Postgrad. Courses Am. Assn. Study Liver Dis., Dallas, TX (Nov. 5-9, 1999)(Abstract 572).
Felker et al., "The Rate of Transfer of Unesterified Cholesterol from Rat Erythrocytes to Emulsions Modeling Nascent Triglyceride-Rich Lipoproteins and Chylomicrons Depends on the Degree of Fluidity of the Surface," J. Nutritional Biochem. 4(1):630-634 (1993).
Ferenci et al, "Combination of interferon (IFN) induction therapy and ribavirin in chronic hepatitis C," Prog. Abstr. Dig. Dis. Week 2000, San Diego, CA (May 21-24, 2000) (Abstract 977).
Fontaine et al., "Recovery from chronic hepatitis C in long-term responders to ribarivin plus interferon α," Lancet 356(9223):41 (Jul. 2000).
Franchetti et al., "Furanfurin and Thiophenfurin: Two Novel Tiazofurin Analogues. Synthesis, Structure, Antitumor Activity, and Interactions with Inosine Monophosphate Dehydrogenase," J. Medicinal Chem. 38(19):3829-3837 (1995).
Fujii et al., "Effect of phosphatidylcholine on Skin Permeation of Indomethacin from gel prepared with Liquid Paraffin and Hydrogenated Phospholipid," Int'l J. Pharmaceutics 222(1):57-64 (2001).
Fujii et al., "Enhancement of skin permeation of miconazole by phospholipid and dodecyl 2-(N, N-dimethylamino) propionate (DDAIP)," Int'l J. Pharmaceutics 234(1-2):121-128 (2002).
Luft et al., "Electro-osmotic valve for the controlled administration of drugs," Med. & Biological Engineering & Computing 45-50 (Jan. 1978) (non-English with English abstract).

(56) References Cited

OTHER PUBLICATIONS

Gan to Kagaku Ryoho, "Phase II study of recombinant leukocyte A interferon (Ro22-8181) in malignant brain tumors," Cancer & Chemotherapy 12(4):913-920 (Apr. 1985) (non-English with English abstract).
Gappa et al., "Juvenile laryngeal papillomatosis—a case report," Pneumologie 45(11):936-938 (Nov. 1991) (XP009079028) (non-English with English abstract).
Gause et al., "Phase I study of subcutaneously administered interleukin-2 in combination with interferon alfa-2a in patients with advanced cancer," J. Clin. Oncol. 14(8):2234-2241 (Aug. 1996).
Ghiglione et al., "How glucagon-like is glucagon-like peptide-1?" Diabetologia 27:599-600 (1984).
Glue et al., "A dose-ranging study of Peg-intron and ribavirin in chronic hepatitis C—safety, efficacy, and virological rationale," Prog. Abstr. 50th Annu. Mtg. Postgrad. Courses Am. Assn. Study Liver Dis., Dallas, TX(Nov. 5-9, 1999)(Abstract 571).
Goke et al., "Exendin-4 is a high potency agonist and truncated exendin-(9-39)-amide an antagonist at the glucagon-like peptide 1-(7-36)-amide receptor of insulin-secreting beta-cells," J. Biol. Chem., 268(26):19650-19655 (1993).
Gonzales et al., "Randomized controlled trial including an initial 4-week 'induction' period during one year of high-dose interferon α-2B treatment for chronic hepatitis C," Prog. Abstr. Dig. Dis. Week 2000, San Diego, CA (May 21-24, 2000) (Abstract 975).
Gosland et al., "A phase I trial of 5-day continuous infusion cisplatin and interferon alpha," Cancer Chemother. Pharmacol. 37(1-2):39-46 (1995).
Grant et al., "Combination therapy with interferon-α plus N-acetyl cysteine for chronic hepatitis C: a placebo controlled double-blind multicentre study," J. Med. Virol. 61(4):439-442 (Aug. 2000).
Gutniak et al., "Antidiabetogenic effect of glucagon-like peptide-1 (7-36)amide in normal subjects and patients with diabetes mellitus," N. Engl. J. Med., 326(20):1316-1322 (1992).
Hageman, "The Role of Moisture in Protein Stability," Drug Dev. & Ind. Pharm. 14(14):2047-2070 (1988).
Heathcote et al., "Peginterferon alfa-2a in Patients With Chronic Hepatitis C and Cirrhosis," New England J. Med. 343(23):1673-1680 (2000).
Heim et al., "Intracellular signaling and antiviral effects of interferons," Dig. Liver Dis. 32(3):257-263 (Apr. 2000).
Heinrich et al., "Pre-proglucagon messenger ribonucleic acid: nucleotide and encoded amino acid sequences of the rat pancreatic complementary deoxyribonucleic acid," Endocrinol., 115:2176-2181 (1984).
Hellstrand et al., "Histamine and cytokine therapy," Acta Oncol. 37(4):347-353 (1998).
Hellstrand et al., "Histamine and the response to IFN-α in chronic hepatitis C," Interferon Cytokine Res. 18(1):21-22 (Jan. 1998).
Hellstrand et al., "Histamine in immunotherapy of advanced melanoma: a pilot study," Cancer Immunol Immunother. 39(6):416-419 (Dec. 1994).
Hisatomi et al., "Toxicity of polyoxyethylene hydrogenated castor oil 60 (HCO-60) in experimental animals," J. Toxicol. Sci., 18(3):1-9 (1993).
Hodoshima et al., "Lipid nanoparticles for delivering antitumor drugs," International Journal of Pharmaceutics, 146(1):81-92 (1997).
Hoffmann-La Roche Inc., Pegasys® (peginterferon alfa-2a), 15 pages (2002).
Horton et al., "Antitumor effects of interferon-omega: in vivo therapy of human tumor xenografts in nude mice" Cancer Res 59(16):4064-4068 (Aug. 1999).
Hubel et al., "A phase I/II study of idarubicin, dexamethasone and interferon-alpha (1-Dexa) in patients with relapsed or refractory multiple myeloma" Leukemia 11 Suppl 5:S47-S51 (Dec. 1997).
Iacobelli et al., "A phase I study of recombinant interferon-alpha administered as a seven-day continuous venous infusion at circadian-rhythm modulated rate in patients with cancer," Am. J. Clin. Oncol. 18(1):27-31 (1995).

IFNB Multiple Sclerosis Study Group, "Interferonβ-1b is effective in relapsing-remitting multiple sclerosis," Neurology 43(4):655-667 (Apr. 1993).
Intermune® Inc., Infergen® (Interferon alfacon-1), 5 pages (2002).
"Introduction to Antibodies", http://www.chemicon.com/resource/ANT101/a1.asp, 8 pages (retrieved May 2, 2007).
Isaacs et al., "Virus interference. I. The interferon," Pro. R. Soc. Lond. B. Biol. Sci. 147:258-267 (1957).
Jain et al., "Controlled delivery of drugs from a novel injectable in situ formed biodegradable PLGA microsphere system," J. Microencapsulation 17(3):343-362 (2000).
Jordan et al., "Guidelines for Antiemetic Treatment of Chemotherapy-Induced Nausea and Vomiting: Past, Present and Future Recommendations," The Oncologist 12(9):1143-1150 (2007).
Kabalnov et al., "Macroemulsion type and stability of alkane-water-phospholipid systems," Abstracts of Papers, Part 1, 210th ACS National Meeting, 0-8412-3222-9, American Chemical Society, Chicago, IL (Aug. 20-24, 1995) (Abstract only).
Kabalnov et al., "Phospholipids as Emulsion Stabilizers.2. Phase Behavior Versus Emulsion Stability," Journal of Colloid and Interface Science 184(1):227-235 (1996).
Khalili et al., "Interferon and ribavirin versus interferon and amantadine in interferon nonresponders with chronic hepatitis C," Am. J. Gastroenterol. 95(5):1284-1289 (May 2000).
Kildsig et al., "Theoretical Justification of Reciprocal Rate Plots in Studies of Water Vapor Transmission through Films," J. Pharma. Sci. 29(11):1634-01637 (Nov. 17, 1970).
Kirkwood et al., "Interferon alfa-2b adjuvant therapy of high-risk resected cutaneous melanoma: The Eastern Cooperative Oncology Group Trial EST 1684," J. Clin. Oncol. 14(1):7-17 (1996).
Kita et al., "Characterization of a polyethylene glycol conjugate of recombinant human interferon-γ," Drug Des. Deliv. 6(3):157-0167 (Sep. 1990).
Knepp et al, "Identification of antioxidants for prevention of peroxide-mediated oxidation of recombinant human ciliary neurotrophic factor and recombinant human nerve growth factor," J. Pharm. Sci. Tech. 50(3):163-171 (1996).
Knepp et al., "Stability of nonaqueous suspension formulations of plasma derived factor IX and recombinant human alpha interferon at elevated temperatures," Pharma. Res. 15(7):1090-1095 (1998).
Knobler et al., "Systemic α-interferon therapy of multiple sclerosis," Neurology 34(10):1273-1279 (Oct. 1984).
Kovacevic et al., "Treatment of chronic viral hepatitis B in secondary membranoproliferative glomerulonephritis using recombinant α-2 interferon," Maksic Dj Vojnosanit. Pregl. 57(2):235-240 (Mar.-Apr. 2000) (non-English with English abstract).
Kracke et al., "Mx proteins in blood leukocytes for monitoring interferon β-1b therapy in patients with MS," Neurology 54(1):193-199 (Jan. 2000).
Kronenberger et al., "Influence of interferon-α on CD82-expression in HCV-positive patients," Prog. Abstr. Dig. Dis. Week 2000, San Diego, CA (May 21-24, 2000) (Abstract 976).
Krown et al., "Interferons and interferon inducers in cancer treatment," Semin. Oncol. 13(2):207-217 (1986).
Kubes et al., "Cross-species antiviral and antiproliferative activity of human interferon-ω," J. Interferon Res. 14:57-59 (1994).
Kunzi et al., "Role of interferon-stimulated gene ISG-15 in the interferon-ω-mediated inhibition of human immunodeficiency virus replication," J. Interferon Cytokine Res. 16(11):919-927 (Nov. 1996).
Larsson, "Stability of emulsions formed by polar lipids," Progress in the Chemistry of Fats and Other Lipids 16:163-0169 (1978).
Lee et al., "Dynamics of hepatitis C virus quasispecies turnover during interferon-A treatment," Prog. Abstr. Dig. Dis. Week 2000, San Diego, CA (May 21-24, 2000) (Abstract 974).
Lee, "Therapy of hepatitis C: interferon alfa-2A trials," Hepatology 26: 89S-95S (Sep. 1997) (XP000981288).
Lopez et al., "Mammalian pancreatic preproglucagon contains three glucagon-related peptides," Proc. Natl. Acad. Sci. USA, 80(18):5485-5489 (1983).

(56) References Cited

OTHER PUBLICATIONS

Lukaszewski et al., "Pegylated α interferon is an effective treatment for virulent Venezuelan equine encephalitis virus and has profound effects on host immune response to infection," J. Virol. 74(11):5006-5015 (Jun. 2000).
Lund et al., "Pancreatic preproglucagon cDNA contains two glucagon-related coding sequences arranged in tandem," Proc. Natl. Acad. Sci. USA, 79(2):345-349 (1982).
Lundberg, "A submicron lipid emulsion coated with amphipathic polyethylene glycol for parenteral administration of paclitaxel (Taxol)," J. Pharm. & Pharmacol. 49(1):16-21 (1997).
Magnuson et al. "Enhanced recovery of a secreted mammalian protein from suspension culture of genetically modified tobacco cells," Protein Expression & Purification 7:220-228 (1996).
Malley et al., "Chronic Toxicity and Oncogenicity of N-Methylpyrrolidone (Nmp) in Rats and Mice by Dietary Administration," Drug Chem Toxicol. 24(4):315-38 (Nov. 2001).
Manning et al, "Stability of protein pharmaceuticals," Pharm. Res. 6(11):903-918 (1989).
Marincola et al., "Combination therapy with interferon alfa-2a and interleukin-2 for the treatment of metastatic cancer," J. Clinical Oncol. 13(5):1110-1122 (1995) (XP009078965).
Massey, "Interaction of vitamin E with saturated phospholipid bilayers," Biochem. & Biophys. Res. Comms. 106(3):842-847 (1982).
McHutchison et al., "Interferon α-2b alone or in combination with ribavirin as initial treatment for chronic hepatitis C," N. Engl. J. Med. 339(21):1485-1492 (Nov. 1998).
McHutchison et al., "Open-label phase 1B study of hepatitis C viral dynamics with omega interferon treatment," Hepatology 34(4):A333 (Oct. 1, 2001) (XP004716177) (Abstract Only).
Meier et al., "The glucagon-like peptide-1 metabolite GLP-1-(9-36) amide reduces postprandial glycemia independently of gastric emptying and insulin secretion in humans," Am. J. Physiol. Endocrinol. Metab., 290(6):E1118-E1123 (2006).
Merad et al., "Generation of monocyte-derived dendritic cells from patients with renal cell cancer: modulation of their functional properties after therapy with biological response modifiers (IFN-α plus IL-2 and IL-12)," J. Immunother. 23(3):369-378 (May-Jun. 2000).
Milella et al., "Neutralizing antibodies to recombinant α-interferon and response to therapy in chronic hepatitis C virus infection," Liver 13(3):146-150 (Jun. 1993).
Mohler, "Primer on electrodeposited coatings," Materials Engineering 5:38-45 (1972).
Mojsov, "Structural requirements for biological activity of glucagon-like peptide-I," Int. J. Peptide Protein Research, 40:333-343 (1992).
Morgan, "Structure and Moisture Permeability of Film-Forming Poloyers," Ind. Eng. Chem. 45(10):2296-2306 (1953).
Motzer et al., "Phase I trial of 40-kd branched pegylated interferon alfa-2a for patients with advanced renal cell carcinoma," J. Clinical Oncol. 19(5):1312-1319 (2001).
Nauck et al., "Normalization of fasting glycaemia by intravenous GLP-1 ([7-36 amide] or [7-37]) in type 2 diabetic patients," Diabet. Med., 15(11):937-945(1998).
Neumann et al., "Hepatitis C Viral Dynamics In Vivo and the Antiviral Efficacy of Interferon-alpha Therapy," Science 282:103-107 (Dec. 1998).
Nieforth et al., "Use of an indirect pharmacodynamic stimulation model of MX protein induction to compare in vivo activity of interferon-α-2a and a polyethylene glycol-modified derivative in healthy subjects," Clin. Pharmacol. Ther. 59(6):636-646 (Jun. 1996).
Norden et al., "Physicochemical characterization of a drug-containing phospholipid-stabilized o / w emulsion for intravenous administration," Eur. J. Pharm. Sci. 13(4):393-401 (2001).
Olaso et al., "Early prediction of lack of response to treatment with interferon and interferon plus ribavirin using biochemical and virological criteria in patients with chronic hepatitis C," Esp. Quimioter. 12(3):220-228 (Sep. 1999) (non-English with English abstract).
Ortiz et al., "A differential scanning calorimetry study of the interaction of α-tocopherol with mixtures of phospholipids," Biochim et Biophys Acta 898(2):214-222 (1987).
Panitch, "Interferons in multiple sclerosis," Drugs 44(6):946-962 (Dec. 1992).
Patzelt et al., "Identification and processing of proglucagon in pancreatic islets," Nature, 282:260-266 (1979).
Peterson et al., "Zucker Diabetic Fatty Rat as a Model for Non-insulin-dependent Diabetes Mellitus," ILAR Journal, 32(3):16-19 (1990).
Peterson et al., "Neuropathic complications in the Zucker diabetic fatty rat (ZDF/Drt-fa)," Frontiers in diabetes research. Lessons from Animal Diabetes III, Shafrir, E. (ed.), pp. 456-458, Smith-Gordon, London (1990).
Pimstone et al., "High dose (780 MIU/52 weeks) interferon monotherapy is highly effective treatment for hepatitis C," Prog. Abstr. Dig. Dis. Week 2000, San Diego, CA (May 21-24, 2000) (Abstract 973).
Plauth et al, "Open-label phase II study of omega interferon in previously untreated HCV infected patients," Hepatology 34(4):A331 (Oct. 1, 2001) (XP004716169) (Abstract Only).
Plauth et al, "Open-label study of omega interferon in previously untreated HCV-infected patients," J. Hepatology 36(Supp. 1):125 (Apr. 2002) (XP002511882) (Abstract Only).
Pohl et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J. Biol. Chem., 273(16):9778-9784 (1998).
Poynard et al., "Is an 'a la carte' combined interferon α 2b plus ribavirin possible for the first line treatment in patients with chronic hepatitis C," Hepatology 31(1):211-218 (Jan. 2000).
Poynard et al., "Randomized trial of interferon α 2b plus ribavirin for 48 weeks or for 24 weeks versus interferon α 2b plus placebo for 48 weeks for the treatment of chronic infection with hepatitis C virus," Lancet 352(9138):1426-1432 (Oct. 1998).
"Intarcia Presents Positive ITCA 650 Phase 2 Study Results for Type 2 Diabetes at EASD," Intarcia Therapeutics, Inc. (Sep. 22, 2010) (Press Release).
Quesada et al., "Interferons in Hematological Malignancies", eds. Baron et al., U. Tex. 487-495 (1987).
Quintanar-Guerrero et al., "Applications of the ion-pair concept to hydrophilic substances with special emphasis on peptides," Pharm. Res. 14(2):119-127 (1997).
Rajkumar et al., "Phase I evaluation of radiation combined with recombinant interferon alpha-2a and BCNU for patients with high-grade glioma," Int'l J. Radiat. Oncol. Biol. Phys. 40(2):297-302 (Jan. 15, 1998).
Roche Pharmaceuticals, Roferon®-A (Interferon alfa-2a, recombinant), 22 pages (2003).
Roff et al., "Handbook of Common Polymers", Cleveland Rubber Co. 72 pages (1971).
Rogers et al., "Permeability Valves," Ind. & Eng. Chem. 49(11):1933-1936 (Nov. 17, 1957).
Roman et al., "Cholestasis in the rat by means of intravenous administration of cyclosporine vehicle, Cremophor EL," Transplantation 48(4):554-558 (1989).
Roth et al., "High Dose Etretinate and Interferon-alpha—A Phase I Study in Squamous Cell Carcinomas and Transitional Cell Carcinomas," Acta Oncol. 38(5):613-617 (1999).
Roth et al., "Combination therapy with amylin and peptide YY[3-36] in obese rodents: anorexigenic synergy and weight loss additivity," Endocrinol. 148(12):6054-61 (Dec. 2007).
Schepp et al., "Exendin-4 and exendin-(9-39)NH2: agonist and antagonist, respectively, at the rat parietal cell receptor for glucagon-like peptide-1-(7-36)NH2," Eur. J. Pharmacol., 269(2):183-191 (1994).
Schering Corp., Intron® A for Injection, 6 pages (2001).
Schering Corp., PEG-Intron™ (Peginterferon alfa-2b) Powder for Injection, 29 pages (2003).
Schmalfub et al., "Modification of drug penetration into human skin using microemulsions," J. Controlled Release 46(3):279-285 (1997).
Sen et al., "The interferon system: a bird's eye view of its biochemistry," J. Biol. Chem. 267(8):5017-5020 (Mar. 1992).

(56) References Cited

OTHER PUBLICATIONS

Shiffman et al., "A decline in HCV-RNA level during interferon or interferon/ribavirin therapy in patients with virologic nonresponse is associated with an improvement in hepatic histology," Prog. Abstr. 50th Annu. Mtg. Postgrad. Courses Am. Assn. Study Liver Dis., Dallas, TX (Nov. 5-9, 1999) (Abstract 567).
Shima et al., "Serum total bile acid level as a sensitive indicator of hepatic histological improvement in chronic hepatitis C patients responding to interferon treatment," J. Gastroenterol. Hepatol. 15(3):294-299 (Mar. 2000).
Shiratori et al., "Histologic improvement of fibrosis in patients with hepatitis C who have sustained response to interferon therapy," Ann. Int. Med. 132(7):517-524 (Apr. 2000).
Simon et al., "A longitudinal study of T1 hypointense lesions in relapsing MS: MSCRG trial of interferon β1a," Neurology 55(2):185-192 (Jul. 2000).
Sparks et al., "Lipoprotein alterations in 10- and 20-week-old Zucker diabetic fatty rats: hyperinsulinemic versus insulinopenic hyperglycemia," Metabolism, 47(11):1315-1324 (1998).
Sulkowski et al., "Pegylated Interferon Alfa-2A (Pegasys™) and Ribavirin Combination Therapy for Chronic Hepatitis C: A Phase II Open-Label Study," Gastroenterology 118(4, Supp. 2) (2000) (Abstract 236).
Sulkowski et al., "Peginterferon-α-2a (40kD) and ribavirin in patients with chronic hepatitis C: a phase II open label study," Biodrugs 16(2):105-109 (2002).
Talpaz et al., "Phase I study of polyethylene glycol formulation of interferon alpha-2B (Schering 54031) in Philadelphia chromosome-positive chronic myelogenous leukemia," Blood 98(6):1708-1713 (2001).
Talsania et al., "Peripheral exendin-4 and peptide YY(3-36) synergistically reduce food intake through different mechanisms in mice," Endocrinology 146(9):3748-56 (Sep. 2005).
Tanaka et al., "Effect of interferon therapy on the incidence of hepatocellular carcinoma and mortality of patients with chronic hepatitis C: a retrospective cohort study of 738 patients," Int. J. Cancer 87(5):741-749 (Sep. 2000).
Tong et al., "Prediction of response during interferon α 2b therapy in chronic hepatitis C patients using viral and biochemical characteristics: a comparison," Hepatology 26(6):1640-01645 (Dec. 1997).
Touza Rey et al., "The clinical response to interferon-γ in a patient with chronic granulomatous disease and brain abscesses due to Aspergillus fumigatus," Ann. Med. Int. 17(2):86-87 (Feb. 2000).
Trudeau et al., "A phase I study of recombinant human interferon alpha-2b combined with 5-fluorouracil and cisplatin in patients with advanced cancer," Cancer Chemother. Pharmacol. 35(6):496-500 (1995).
Tseng et al., "Glucose-dependent insulinotropic peptide: structure of the precursor and tissue-specific expression in rat," PNAS USA, 90(5):1992-1996 (1993).
Tsung et al., "Preparation and Stabilization of Heparin/Gelatin Complex Coacervate Microcapsules," J. Pharm. Sci. 86(5):603-7 (May 1997).
Unniappan et al., "Effects of dipeptidyl peptidase IV on the satiety actions of peptide YY," Diabetologia; Clinical and Experimental Diabetes and Metabolism 49(8):1915-1923 (Jun. 27, 2006).
Vokes et al., "A phase I trial of concomitant chemoradiotherapy with cisplatin dose intensification and granulocyte-colony stimulating factor support for advanced malignancies of the chest," Cancer Chemother. Pharmacol. 35(4):304-312 (1995).
Vrabec, "Tympanic membrane perforations in the diabetic rat: a model of impaired wound healing," Otolaryngol. Head Neck Surg., 118(3 Pt. 1):304-308 (1998).
Wang et al., "Preferential interaction of α-tocopherol with phosphatidylcholines in mixed aqueous dispersions of phosphatidylcholine and phosphatidylethanolamine," Eur. J. Biochem. 267(21):6362-6368 (2000).
Wang et al., "Ripple phases induced by α-tocopherol in saturated diacylphosphatidylcholines," Archives of Biochem. & Biophys. 377(2):304-314 (2000).
Wang et al., "The distribution of α-tocopherol in mixed aqueous dispersions of phosphatidylcholine and phosphattidylethanolamine," Biochimica et Biophysica Acta—Biomembranes 1509(1-2):361-372 (2000).
Wang et al, "Parenteral formulations of proteins and peptides: stability and stabilizers," J. Parenter. Sci. Technol. 42(2S):S4-S26 (1988).
Weinstock-Guttman et al., "What is new in the treatment of multiple sclerosis?" Drugs 59(3):401-410 (Mar. 2000).
Weissmann et al., "The interferon genes," Prog. Nucleic Acid Res. Mol. Biol. 33:251-300 (1986).
Wright et al., "Preliminary experience with α-2b-interferon therapy of viral hepatitis in liver allograft recipients," Transplantation 53(1):121-123 (Jan. 1992).
Young et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes, 48(5):1026-1034 (1999).
Younossi et al., "The role of amantadine, rimantadine, ursodeoxycholic acid, and NSAIDs, alone or in combination with α interferons, in the treatment of chronic hepatitis C," Semin. Liver Dis. 19(Supp. 1):95-102 (1999).
Yu et al., "Preparation, characterization, and in vivo evaluation of an oil suspension of a bovine growth hormone releasing factor analog," J. Pharm. Sci. 85(4):396-401 (1996).
Zeidner et al., "Treatment of FeLV-induced immunodeficiency syndrome (feLV-FAIDS) with controlled release capsular implantation of 2',3'-dideoxycytidine," Antivir. Res. 11(3):147-0160 (Apr. 1989).
Zein, "Interferons in the management of viral hepatitis," Cytokines Cell Mol. Ther. 4(4):229-241 (Dec. 1998).
Zeuzem et al., "Peginterferon Alfa-2a in Patients with Chronic Hepatitis C," New Engl. J. Med. 343(23):1666-1672 (2000).
Zeuzem et al., "Hepatitis C virus dynamics in vivo: effect of ribavirin and interferon α on viral turnover," Hepatology 28(1):245-252 (Jul. 1998).
Zhang et al., "Report on Large Dosage Interferon to Treat 30 Cases of Viral Encephalitis," J. Clinical Pediatrics 14(2):83-84 (1996).
Zhang et al, "A new strategy for enhancing the stability of lyophilized protein: the effect of the reconstitution medium on keratinocyte growth factor," Pharm. Res. 12(10):1447-1452 (1995).
Zheng et al. "Therapeutic Effect of Interferon Varied Dose in Treating Virus Encephalitis," Beijing Med. J. 13(2):80-81 (1998).
Ziesche et al., "A preliminary study of long-term treatment with interferon γ-1b and low-dose prednisolone in patients with idiopathic pulmonary fibrosis," New Engl. J. Med. 341(17):1264-1269 (Oct. 1999).
Sanofi-Aventis U.S. LLC, Prescribing Information for ADLYXIN® (Lixisenatide) Injection, for Subcutaneous Use, rev. Jul. 2016, 31 pages.
Amylin Pharmaceuticals, Inc., Prescribing Information for BYETTA® (Exenatide) Injection, rev. Oct. 2009, 34 pages.
Astrazeneca Pharmaceuticals LP, Prescribing Information for BYDUREON® (Exenatide Extended-Release for Injectable Suspension), rev. Mar. 2015, 60 pages.
Novo Nordisk A/S, Prescribing Information for Victoza® (Liraglutide [rDNA Origin] Injection), Solution for Subcutaneous Use, v. 1, Jan. 2010, 23 pages.
Glaxosmithkline LLC, Prescribing Information for TANZEUM® (Albiglutide) for Injection, for Subcutaneous Use, rev. Jun. 2014, 55 pages.
Eli Lilly & Company, Prescribing Information for TRULICITY® (Dulaglutide) Injection, for Subcutaneous Use, rev. Mar. 2015, 19 pages.
Akers, et al., "Formulation Design and Development of Parenteral Suspensions," Journal of Parenteral Science & Technology, 41(3): 88-96 (1987).
Alonso, et al., "Determinants of Release Rate of Tetanus Vaccine from Polyester Microspheres," Pharmaceutical Research, 10(7):945-953 (1993).
Beck, et al., "Poly(dl-lactide-co-glycolide)/norethisterone microcapsules: An injectable biodegradable contraceptive," Biology of Reproduction, 28(1): 186-195 (1983).

(56) References Cited

OTHER PUBLICATIONS

Bodmeier and McGinity, "Solvent selection in the preparation of poly(dl-lactide) microspheres prepared by the solvent evaporation method," International Journal of Pharmaceutics, 43(1-2): 179-186 (Apr. 1988).
Cha and Pitt, "A one-week subdermal delivery system for l-methadone based on biodegradable microcapsules," Journal of Controlled Release, 7: 69-78 (1988).
Cha and Pitt, "The acceleration of degradation-controlled drug delivery from polyester microspheres," Journal of Controlled Release, 8: 259-265 (1989).
Cohen, et al., "Controlled delivery systems for proteins based on poly(lactic/glycolic acid) microspheres," Pharmaceutical Research, 8(6): 713-720 (1991).
Conti, et al., "Use of polylactic acid for the preparation of microparticulate drug delivery systems," Journal of Microencapsulation, 9(2): 153-166 (1992).
Hodgman, et al., Eds., Handbook of Chemistry and Physics, 35th Edition, 1024-1025 (1953).
Jalil and Nixon, "Biodegradable poly(lactic acid) and poly(lactide-co-glycolide) microcapsules: Problems associated with preparative techniques and release properties," Journal of Microencapsulation, 7(3): 297-325 (Jul.-Sep. 1990).
Lee and Timasheff, "The stabilization of proteins by sucrose," J. Biological Chem., 256(14): 7193-7201 (Jul. 1981).
Li, et al., "Prediction of solvent removal profile and effect on properties for peptide-loaded PLGA microspheres prepared by solvent extraction/evaporation method," Journal of Controlled Release, 37: 199-214 (1995).
Maa and Hsu, "Liquid-liquid emulsification by static mixers for use in microencapsulation," Journal of Microencapsulation, 13(4): 419-433 (Jul.-Aug. 1996).
Maulding, et al., "Biodegradable microcapsules: Acceleration of polymeric excipient hydrolytic rate by incorporation of a basic medicament," Journal of Controlled Release, 3: 103-117 (1986).
Mehta, et al., "Peptide containing microspheres from low molecular weight and hydrophilic poly(d,l-lactide-co-glycolide)," Journal of Controlled Release, 41: 249-257 (1996).
Sah, et al., "A novel method of preparing PLGA microcapsules utilizing methylethyl ketone," Pharmaceutical Research, 13(3): 360-367 (1996).
Sato, et al., "Porous biodegradable microspheres for controlled drug delivery. I. Assessment of processing conditions and solvent removal techniques," Pharmaceutical Research, 5(1): 21-30 (1988).
Szayna, et al., "Exendin-4 decelerates food intake, weight gain, and fat deposition in Zucker rats," Endocrinology, 141(6): 1936-1941 (2000).
Thomasin, et al., "A contribution to overcoming the problem of residual solvents in biodegradable microspheres prepared by coacervation," Eur. J. Pharm. Biopharm., 42(1): 16-24 (1996).
Van Santbrink and Fauser, "Urinary follicle-stimulating hormone for normogonadotropic colomiphene-resistant anovulatory infertility: Prospective, randomized comparison between low dose step-up and step-down dose regimens," J. Clin. Endocrin. Metab., 82(11): 3597-3602 (1997).
Tracy et al., "Factors affecting the degradation rate of poly(lactide-co-glycolide) microspheresin vivo and in vitro." Biomaterials. 20(11:): 1057-1062 (1999).
Ertl et al., "Poly (DL-lactide-co-glycolide) microspheres as carriers for peptide vaccines," Vaccine 14(9):879-885.(1996).
Thompson et al., "Biodegradable microspheres as a delivery system for rismorelin porcine, a porcine-growth-hormone-releasing hormone," Journal of Controlled Release 43(1):9-22 (1997).
Henry et al., "A Randomized, Open-Label, Multicenter, 4-Week Study to Evaluate the Tolerability and Pharmacokinetics of ITCA 650 in Patients With Type 2 Diabetes", Clinical Therapeutics, vol. 35, No. 5, May 2013 (May 2013), pp. 634-645.
Henry et al., "Continuous subcutaneous delivery of exenatide via ITCA 650 leads to sustained glycemic control and weight loss for 48 weeks in metformin-treated subjects with type 2 diabetes", Journal of Diabetes and Its Complications, vol. 28, No. 3, May 2014, pp. 393-398.
Iltz et al., "Exenatide: An incretin mimetic for the treatment of type 2 diabetes mellitus", Clinical Therapeutics, Excerpta Medica, Princeton, NJ, US, vol. 28, No. 5, May 1, 2006, pp. 652-665, XP027906950, ISSN: 0149-2918.
Kothare et al., "Exenatide effects on statin pharmacokinetics and lipid response.", International Journal of Clinical Pharmacology and Therapeutics Feb. 2007, vol. 45, No. 2, pp. 114-120, XP9505794, ISSN: 0946-1965.
Kothare et al., "Effect of exenatide on the pharmacokinetics of a combination oral contraceptive in healthy women: an open-label, randomised, crossover trial", BMC Clinical Pharmacology, Biomed Central, London, GB, vol. 12, No. 1, Mar. 19, 2012, p. 8, XP021095589, ISSN: 1472-6904, DOI: 10.1186/1472-6904-12-8.
Kjems Lise et al., "Treatment with ITCA 650 Does Not affect the Pharmacokinetics (PK) and Pharmacodynamics of a Combination Oral Contraceptive (OC)", Diabetes, vol. 66, No. Suppl. 1, Jun. 1, 2017, pp. A294-A295, & 77th Scientific Sessions of the American-Diabetes-Association; San Deigo, CA, USA; Jun. 9-13, 2017.
Lathia et al., "Effect of ITCA 650 on the PK of Acetaminophen (APAP) and Other Commonly Coadministered Drugs", Diabetes, vol. 66, No. Suppl. 1, Jun. 1, 2017, p. A294 & 77th Scientific Sessions of the American-Diabetes-Association; San Diego, CA, USA; Jun. 9-13, 2017.
International Preliminary Report on Patentability dated Jul. 9, 2019 in related PCT Application No. PCT/US2018/012204 (9 pages).

Statistical Assessment of Drug-drug Interaction of ITCA650 on EE and LNG on Day 28

METHODS COMPRISING CONTINUOUS ADMINISTRATION OF A GLP-1 RECEPTOR AGONIST AND CO-ADMINISTRATION OF A DRUG

CROSS REFERENCE TO RELATED APPLICATIONS

This application claims priority to and the benefit of U.S. Provisional Application Ser. 62/441,833, filed Jan. 3, 2017, which is herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jan. 2, 2018 is named ITCA-052-001US ST25.txt and is 743 bytes in size.

BACKGROUND

By some estimates, over 350 million people worldwide are presently diagnosed with type 2 diabetes mellitus (T2D) and one in three people in the United States will develop T2D in their lifetime. For treatment of this disease, the American Diabetes Association (ADA) recommends metformin as first-line therapy due to its low cost, availability and reasonable efficacy in reducing glycated hemoglobin (HbA1c), despite certain shortcomings associated with this drug. The ADA also recommends potential second-line options, including glucagon-like peptide-1 (GLP-1) receptor agonists, sodium-glucose cotransporter 2 (SGLT2) inhibitors, dipeptidyl peptidase-4 inhibitors (DPP-4), sulfonylureas, thiazolidinediones and insulin. Treatment of T2D with GLP-1 receptor agonist peptides, in particular, has grown. GLP-1 receptor agonists generally provide important effects in subjects beyond blood glucose control, such as effecting weight loss, preserving beta-cell function, and mitigating hypertension, hypoglycemia and/or hyperlipidemia. Methods are presently needed to more fully and properly implement treatment with GLP-1 receptor agonists and better address growing needs of subjects with T2D, obesity or excessive body weight, some of whom must simultaneously manage treatment of unrelated diseases or disorders.

SUMMARY

Periodic and subcutaneous administrations (i.e., injections) of a GLP-1 receptor agonist are presently used to achieve a glucose-dependent increase in insulin in subjects with T2D. The present invention encompasses the recognition of a problem regarding treatment of T2D with GLP-1 receptor agonists. Specifically, injections of certain GLP-1 receptor agonists generally slow gastric emptying and can reduce the extent and rate of absorption of orally administered drugs. Upon injection of certain GLP-1 receptor agonists, co-administration of certain drugs for treatment of diseases other than T2D may require dose adjustment of these drugs (relative to doses prescribed for the drugs when administered alone) or preclude co-administration of certain drugs upon injection of the GLP-1 receptor agonists. Certain injectable GLP-1 receptor agonists have been found to distort areas under the curve (AUC), $C_{max}$, and $T_{max}$ for certain orally available drugs for treatment of diseases, disorders or conditions unrelated to T2D upon co-administration. Consequently, since doses adjustments are often impractical, such drugs must be administered before (e.g., at least one hour prior to) injection of the GLP-1 receptor agonist.

For example, according to prescribing information (PI) for injectable Byetta® (exenatide) for the treatment of T2D, "[oral contraceptive] OC products should be administered at least one hour prior to BYETTA injection." As explained in the PI for Byetta®, co-administration of an oral contraceptive and Byetta® results in decreased $C_{max}$ and delayed $T_{max}$ for the oral contraceptive: "The effect of BYETTA (10 mcg BID) on single and on multiple doses of a combination oral contraceptive (35 mcg ethinyl estradiol plus 150 mcg levonorgestrel) was studied in healthy female subjects. Repeated daily doses of the oral contraceptive (OC) given 30 minutes after BYETTA administration decreased the $C_{max}$ of ethinyl estradiol and levonorgestrel by 45% and 27%, respectively and delayed the $T_{max}$ of ethinyl estradiol and levonorgestrel by 3.0 hours and 3.5 hours, respectively, as compared to the oral contraceptive administered alone. Administration of repeated daily doses of the OC one hour prior to BYETTA administration decreased the mean $C_{max}$ of ethinyl estradiol by 15% but the mean $C_{max}$ of levonorgestrel was not significantly changed as compared to when the OC was given alone."

Also according to prescribing information (PI) for injectable Byetta® (exenatide) for the treatment of T2D, "[a]cetaminophen AUC, $C_{max}$ and $T_{max}$ were not significantly changed when acetaminophen was given 1 hour before BYETTA injection." However, a s explained in the PI for Byetta®, co-administration of a pain reliever such as acetaminophen with Byetta® or after Byetta® injection, results in decreased areas under the curve (AUC) and $C_{max}$, and increases in $T_{max}$, for acetaminophen. "When 1000 mg acetaminophen elixir was given with 10 mcg BYETTA (0 h) and 1 hour, 2 hours, and 4 hours after BYETTA injection, acetaminophen AUCs were decreased by 21%, 23%, 24%, and 14%, respectively; $C_{max}$ was decreased by 37%, 56%, 54%, and 41%, respectively; $T_{max}$ was increased [delayed] from 0.6 hour in the control period to 0.9 hour, 4.2 hours, 3.3 hours, and 1.6 hours, respectively."

Unfortunately, real life circumstances often preclude subjects (i.e., human subjects) from adhering to prescribing information regarding pre-administration of drugs for treatment(s) unrelated to T2D prior to injection of a GLP-1 receptor agonist for the treatment of T2D. GLP-1 receptor agonists include twice-daily injectable Byetta® (exenatide), once-daily injectable Victoza® (liraglutide), once weekly injectable Trulicity® (dulaglutide) and once weekly injectable Ozempic® (semaglutide). Specifically, real life onset of conditions such as pain, heart attack, hypertension, stroke, blood clot, or the need for contraception commonly occur after, sometimes immediately after, bolus injection of a GLP-1 receptor agonist. Yet, when confronted with such circumstances, the subject must delay treatment until one or several hours before administration of the next injection of GLP-1 receptor agonist. Failure to adhere to this prescribing information, as it relates to pre-administration of such drugs before bolus injection of the GLP-1 receptor agonist, puts subjects at risk of effecting suboptimal AUC, $C_{max}$ and/or $T_{max}$ of such drugs.

It has been discovered that continuous administration of GLP-1 receptor agonists, such as exenatide, via an implantable delivery device is not accompanied by either substantial delays in gastric emptying (See FIGS. 1 & 2) or substantial reductions in blood concentrations of glucagon (See FIGS. 3-5). Without being bound by theory, it thus appears that delays in gastric emptying and reductions in blood concentrations of glucagon are substantially attributable to the mode of administration for certain GLP-1 receptor agonists.

It has also been discovered that certain drugs other than those for treating T2D (e.g., drugs for treatment or prevention of pain, conditions associated with heart disease or a heart attack, hypertension, stroke or blood clot, and oral contraceptives) can effectively be co-administered upon continuous administration of a GLP-1 receptor agonist via an implantable delivery device. Therefore, the requirement for pre-administration of certain drugs, relative to injection of the GLP-1 receptor agonist such as exenatide, similarly appear attributable to the mode of administration for the GLP-1 receptor agonist.

Thus, whereas bolus injection of a GLP-1 receptor agonist such as Byetta® require advance oral administration of certain drugs (e.g., for treatment or prevention of pain and oral contraceptives) at least one hour prior to injection of Byetta®, applicants have discovered that such drugs can be orally administered after implantation of an osmotic delivery device and during continuous subcutaneous delivery (e.g., during three, six, twelve, or twenty-four month administration periods) of a GLP-1 analog such as exenatide (e.g., at 20 µg/day or 60 µg/day ITCA-650). This increased versatility of co-administration provides subjects, who have been administered implantable osmotic delivery devices for continuous subcutaneous delivery of a GLP-1 analog, with the option to effectively co-administer orally available drugs (e.g., for treatment of pain, a heart condition, heart attack, hypertension, stroke, and/or preventing a blood clot or providing contraception) at any time during three, six, twelve, or twenty-four month administration period of continuous subcutaneous delivery of the GLP-1 analog.

In certain embodiments, the present invention provides a method for administering to a subject, via an implantable delivery device, a continuous subcutaneous dose of glucagon-like peptide-1 (GLP-1) analog, where the subject is orally co-administered a drug after implantation of the implantable delivery device and during continuous subcutaneous dosing of the GLP-1 analog. In other words, the subject is co-administered the drug following implantation of the implantable delivery device and during three, six, twelve, or twenty-four month administration period of continuous subcutaneous delivery of the GLP-1 analog without resorting to advance administration of the drug prior to administration (i.e., implantation) of the GLP-1 analog.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the invention will be apparent from the following detailed description and claims.

BRIEF DESCRIPTIONS OF THE DRAWINGS

The above and further features will be more clearly appreciated in view of the following detailed description and accompanying drawings.

FIG. 1 is a graph illustrating 0-30-minute increments in plasma glucose levels during test meals for 10-, 20-, 40- and 80 µg/day exenatide treatments, measured before and after 5, 15, and 29 days of treatment. Symbols are group means of individual increments±standard error of the mean (SEM).

FIG. 2 is a graph illustrating dose-responses for 30-minute changes in glucose concentrations during test meals relative to pre-treatment values. Curves for Days 5, 15 and 29 are 3-parameter sigmoids constrained to share a common effective dose causing 50% inhibition ($ED_{50}$). Symbols are group means of individual values±SEM.

Figure 6A:
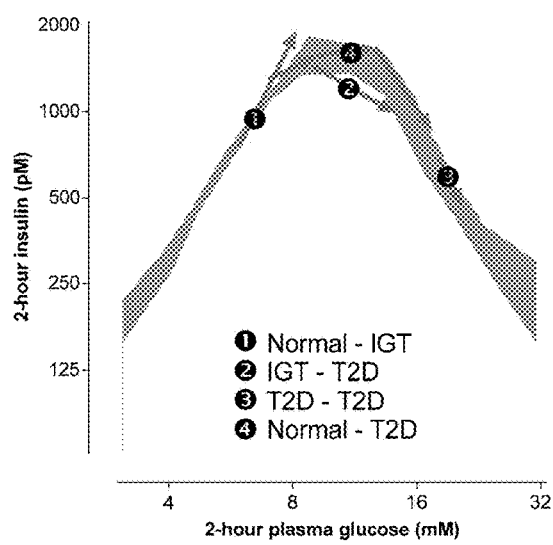

FIG. 6A (left), redrawn from Saad et al., is a graph illustrating changing [insulin] vs [glucose] relationship during the progression from normal glucose tolerance to T2D.

Figure 6B:
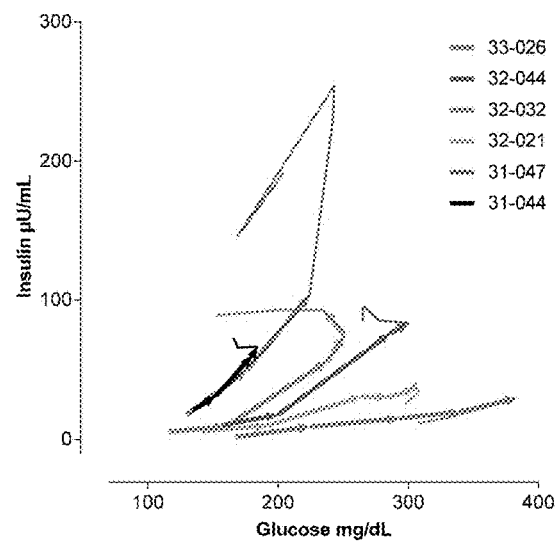

FIG. 6B (right) is a graph that exemplifies the diverse [insulin] vs [glucose] relationships in the current study.

Figure 7:
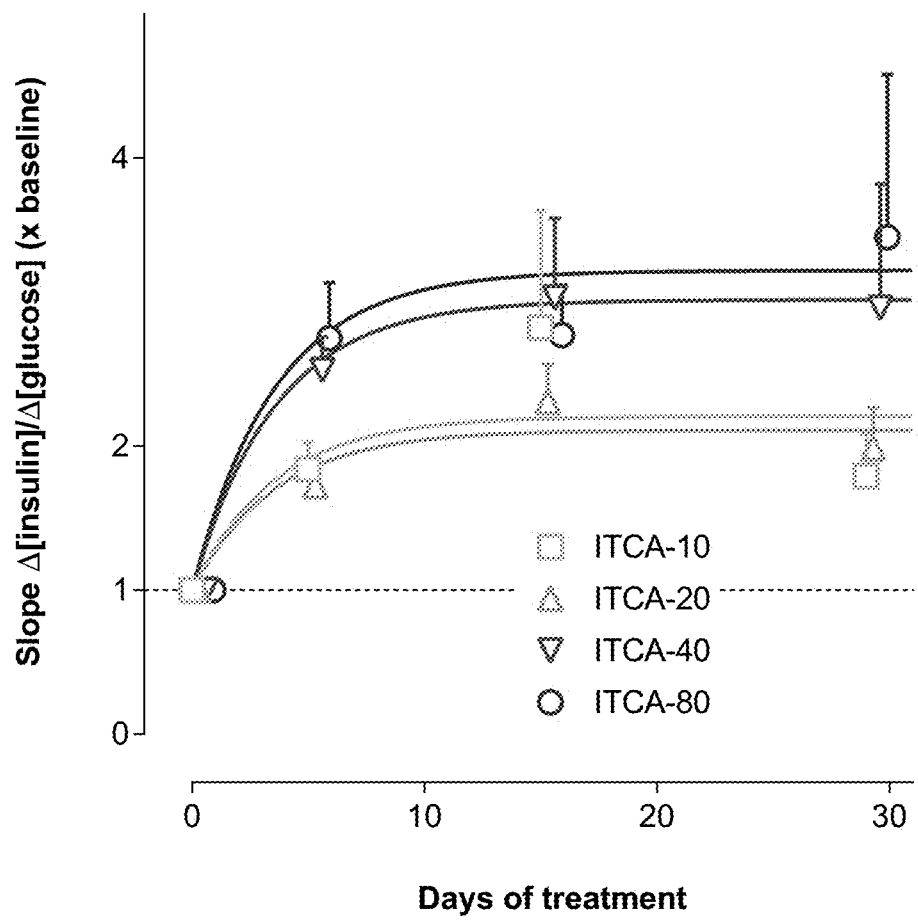

FIG. 7 is a graph illustrating multiples above pre-treatment baseline of best fitting [insulin]×[glucose] slopes. The curves are the best fitting exponential association as a function of duration of treatment.

Figure 8:
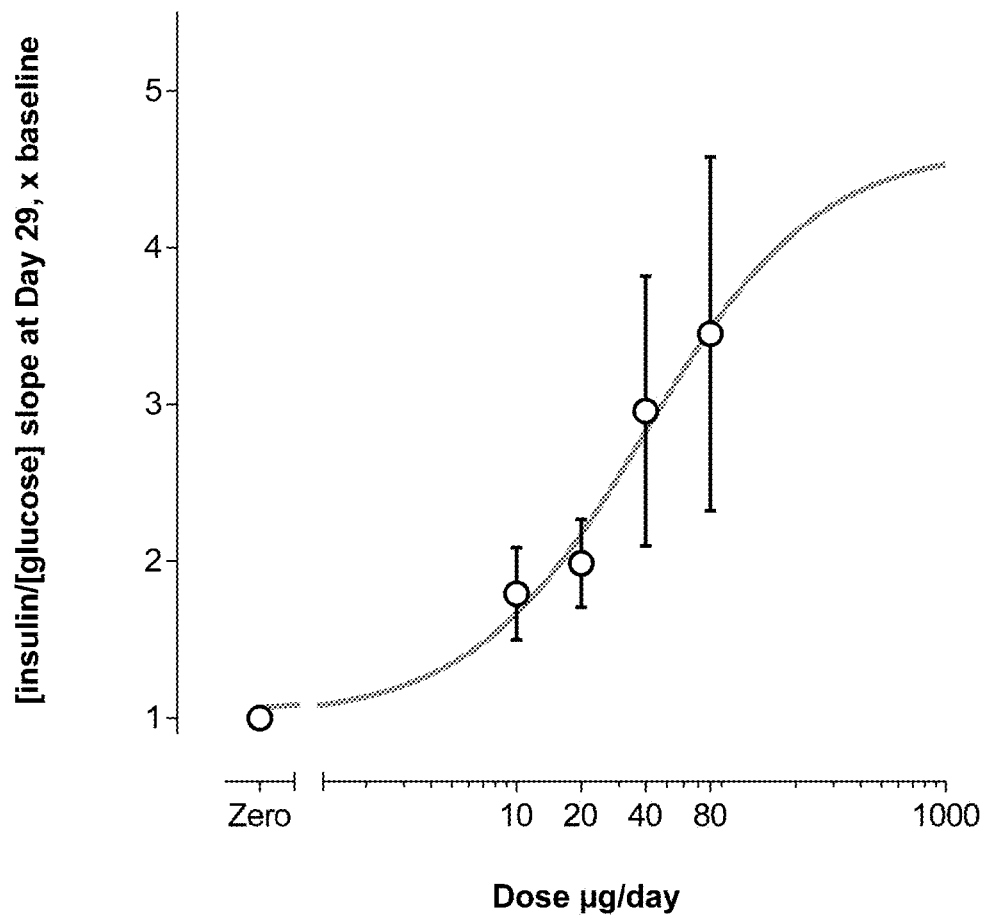

FIG. 8 is a graph illustrating dose response for the effect of ITCA-650 to increase slope of the [insulin]/[glucose] relationship.

Figure 9:
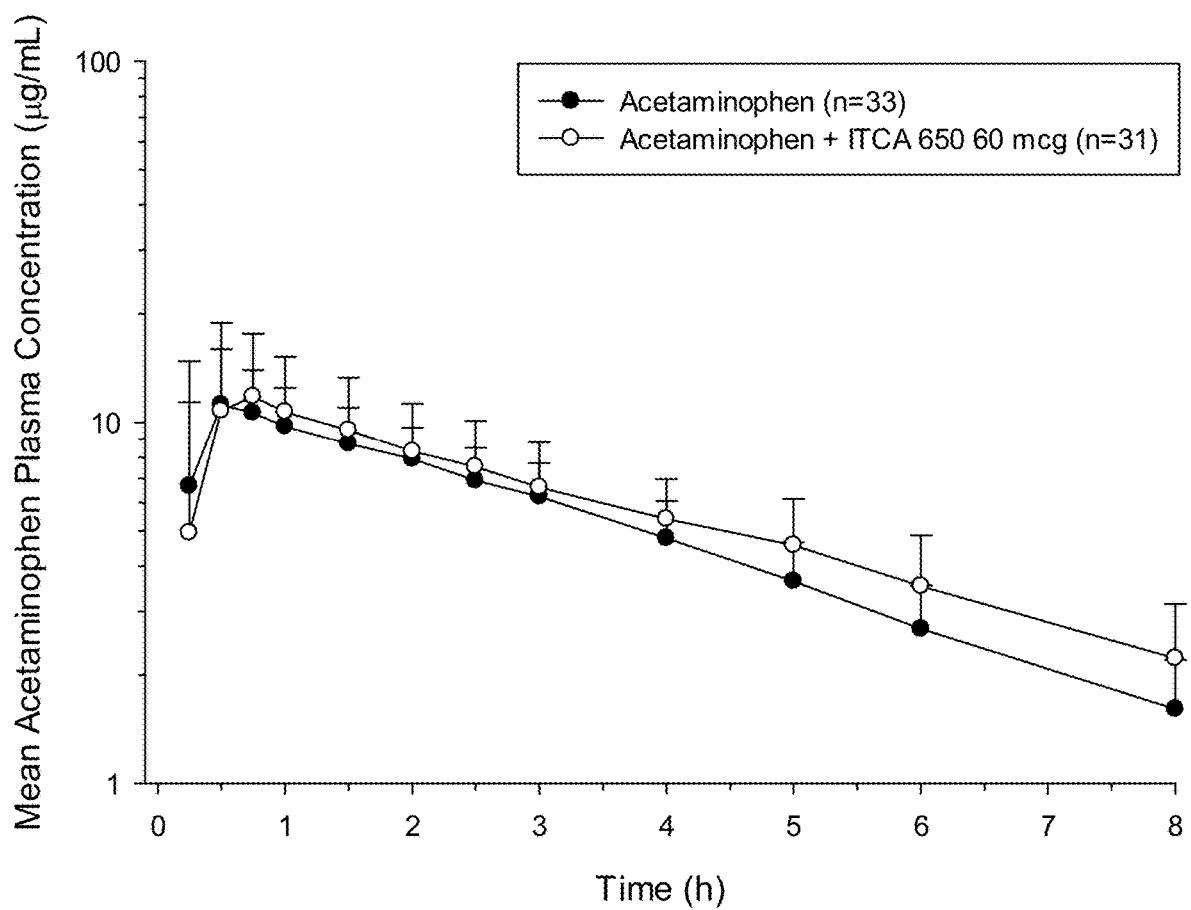

FIG. 9 is a graph illustrating mean plasma concentrations of acetaminophen over time, at day 27, alone and upon co-administration with ITCA-650, during continuous delivery of exenatide via an implanted osmotic delivery device.

Figure 10:
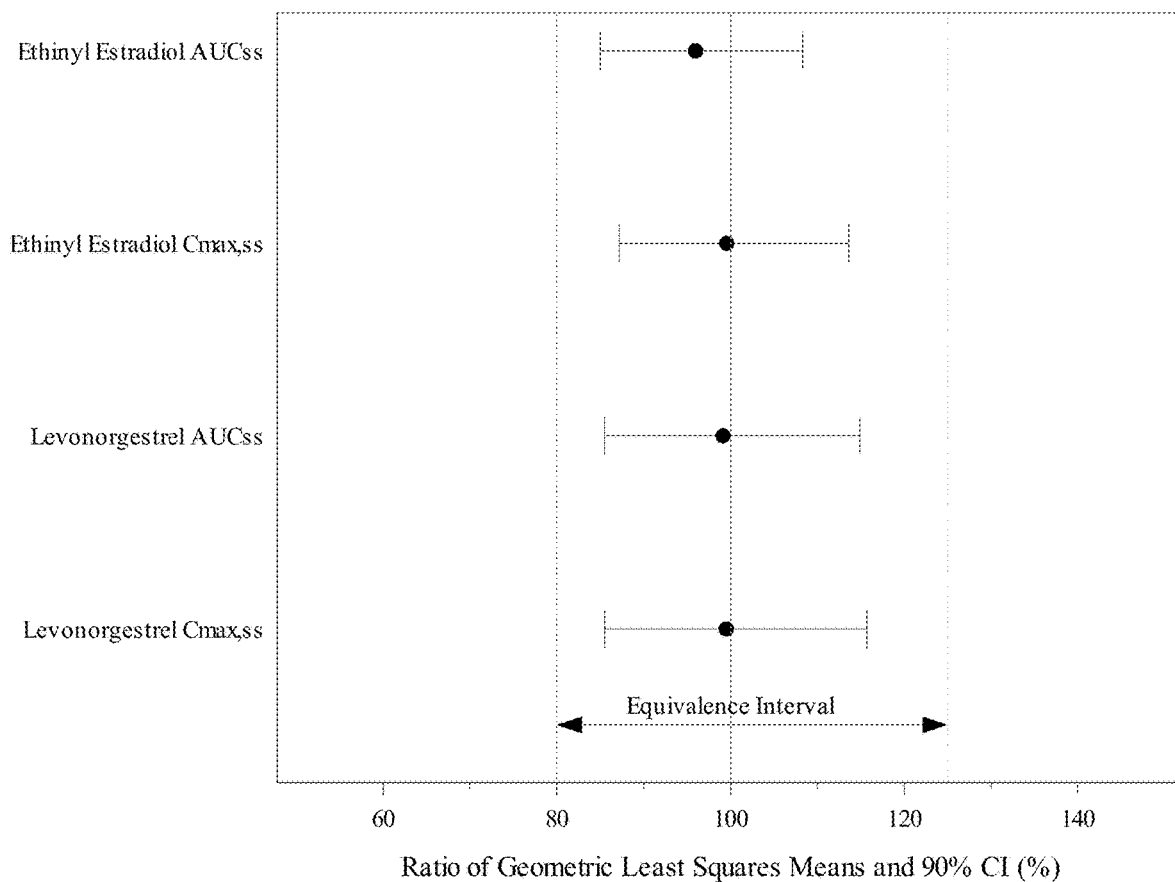

FIG. 10 provides statistical assessments of drug-drug interactions of exenatide and ethinyl estradiol (EE) and levonorgestrel (LNG) from Levora® (OC) during continuous delivery of exenatide via an implanted osmotic delivery device.

Figure 11:
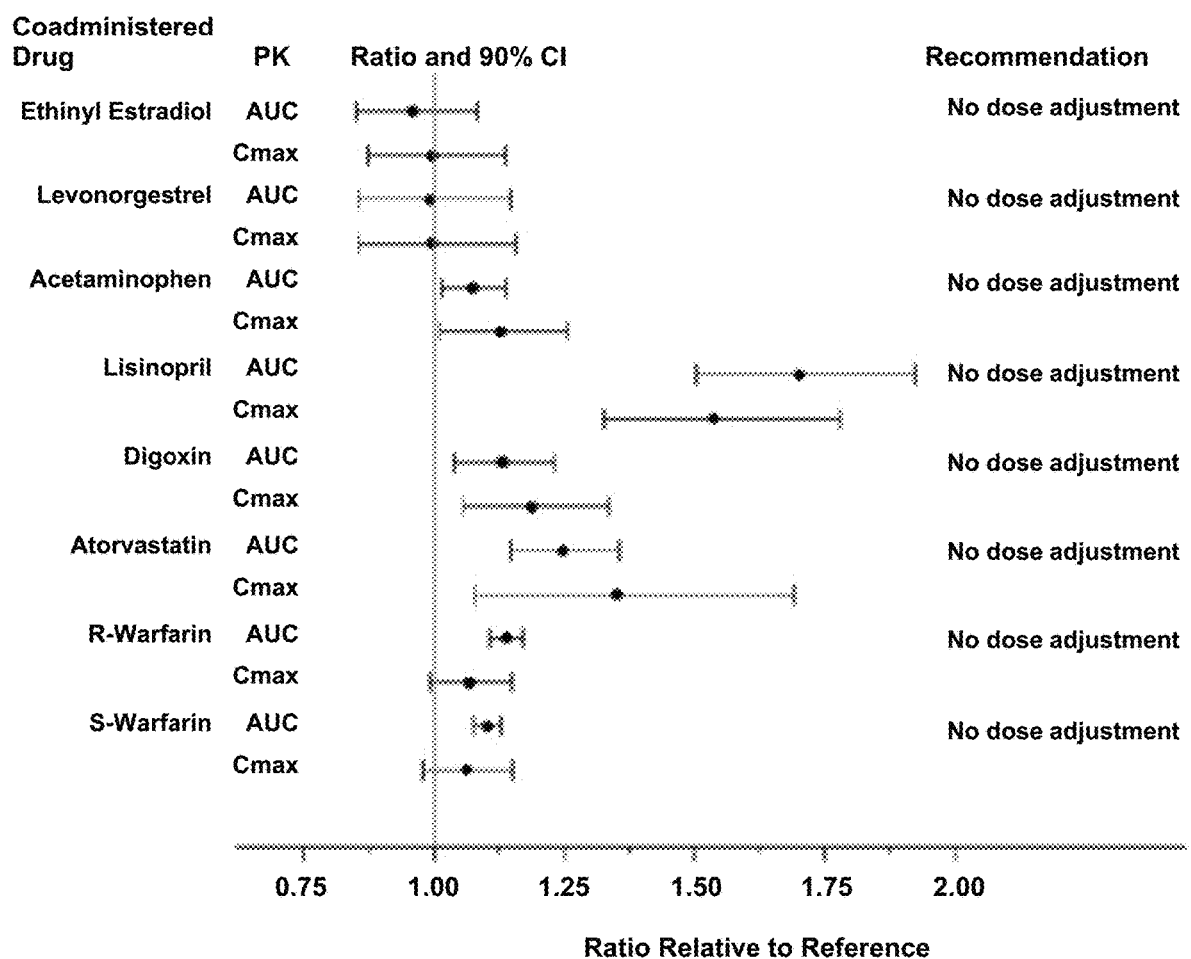

FIG. 11 is a chart that illustrates pharmacokinetic parameters demonstrating that ITCA-650 did not substantially affect pharmacokinetics of certain orally co-administered medications to a clinically relevant degree.

DETAILED DESCRIPTION

Definitions

Glucagon-like peptide-1 (GLP-1) derives from pre-proglucagon, a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. GLP-1 is produced as a 37-amino acid peptide that corresponds to amino acids 72 through 108 of proglucagon (92 to 128 of preproglucagon). GLP-1(7-36) amide or GLP-1(7-37) acid are biologically active forms of GLP-1, that demonstrate essentially equivalent activity at the GLP-1 receptor.

GLP-1 and GLP-1 analogs, acting as agonists at the GLP-1 receptor, have been shown to provide effective hypoglycemic control, e.g., for treating patients with type-2 diabetes. Certain GLP-1 analogs are being sold or are in development for treatment of type-2 diabetes including, e.g., Byetta® & Bydureon BCise® (exenatide), Ozempic® (semaglutide), Victoza® (liraglutide), Adlyxin® (lixisenatide); Tanzeum® (albiglutide), and Trulicity® (dulaglutide).

The term "osmotic delivery device" as used herein typically refers to a device used for delivery of a drug (e.g., an insulinotrophic peptide) to a subject, wherein the device comprises, for example, a reservoir (made, e.g., from a titanium alloy) having a lumen that contains a suspension formulation comprising a drug (e.g., an insulinotrophic peptide) and an osmotic agent formulation. A piston assembly positioned in the lumen isolates the suspension formulation from the osmotic agent formulation. A semi-permeable membrane is positioned at a first distal end of the reservoir adjacent the osmotic agent formulation and a diffusion moderator (which defines a delivery orifice through which the suspension formulation exits the device) is positioned at a second distal end of the reservoir adjacent the suspension formulation. Typically, the osmotic delivery device is implanted within the subject, for example, subdermally or subcutaneously (e.g., in the abdominal area or in the inside, outside, or back of the upper arm). An exemplary osmotic delivery device is the DUROS® delivery device. Examples of terms synonymous to "osmotic delivery device" include but are not limited to "osmotic drug delivery device," "osmotic drug delivery system," "osmotic device," "osmotic delivery device," "osmotic delivery system," "osmotic pump," "implantable drug delivery device," "drug delivery system," "drug delivery device," "implantable osmotic pump," "implantable drug delivery system," and "implantable delivery system." Other terms for "osmotic delivery device" are known in the art. As used herein, "ITCA 650" is an osmotic delivery device comprising exenatide having the amino acid sequence of SEQ ID NO: 1: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly- Ala-Pro-Pro-Pro-Ser-NH$_2$.

The term "continuous delivery" as used herein typically refers to a substantially continuous release of drug from an osmotic delivery device and into tissues near the implantation site, e.g., subdermal and subcutaneous tissues. For example, the osmotic delivery device releases drug essentially at a predetermined rate based on the principle of osmosis. Extracellular fluid enters the osmotic device through the semi-permeable membrane directly into the osmotic engine that expands to drive the piston at a slow and consistent rate of travel. Movement of the piston forces the drug formulation to be released through the orifice of the diffusion moderator. Thus, release of the drug from the osmotic delivery device is at a slow, controlled, consistent rate.

The term "substantial steady-state delivery" as used herein typically refers to delivery of a drug at or near a target concentration over a defined period of time, wherein the amount of the drug being delivered from an osmotic delivery device is substantially zero-order delivery. Substantial zero-order delivery of a therapeutic agent (e.g., an insulinotrophic peptide, preferably, an exenatide) means that the rate of drug delivered is constant and is independent of the drug available in the delivery system; for example, for zero-order delivery, if the rate of drug delivered is graphed against time and a line is fitted to the data the line has a slope of approximately zero, as determined by standard methods (e.g., linear regression).

As used herein, the terms "treatment," "treat," and "treating" refer to reversing, alleviating, ameliorating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "subject," as used herein, means an animal, preferably a mammal, and most preferably a human. The term "subject," as used herein, also means a patient, preferably a human patient suffering from T2D, obesity or in need of weight loss.

As used herein, the term "co-administration" generally refers to separate administration of a drug to a subject during or after bolus injection of GLP-1 receptor agonist to the subject, or separate administration of a drug to a subject during or after insertion in the subject of an osmotic delivery device comprising GLP-1 receptor agonist such as exenatide.

The term "dose adjustment" refers to a change in dosage of a drug for treatment of a disease or disorder other than type-2 diabetes that is made upon co-administration of a GLP-1 receptor agonist, relative to the dosage used upon administration of the drug alone or in the absence of the GLP-1 receptor agonist.

Unless otherwise defined, all technical and scientific terms used herein have the same meaning as commonly understood by one of ordinary skill in the art to which this invention belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

DESCRIPTION OF EXEMPLARY EMBODIMENTS

In one aspect, the present invention provides a method comprising administering to a subject, via an implantable delivery device, a continuous subcutaneous dose of glucagon-like peptide-1 (GLP-1) analog, where the subject is orally co-administered a drug after implantation of the implantable delivery device and during continuous subcutaneous dosing of the GLP-1 analog.

In another aspect, the present invention provides a drug for use in a method of treatment of a subject (e.g., a patient suffering from T2D and/or obesity and/or in need of weight loss), the method comprising administering to the subject (e.g., patient), via an implantable osmotic delivery device, a continuous subcutaneous dose of a glucagon-like peptide-1

(GLP-1) analog; and orally co-administering a drug after implantation of the implantable delivery device and during continuous subcutaneous dosing of the GLP-1 analog.

In some embodiments, the subject is orally co-administered a drug one hour to six months after implantation of the implantable delivery device. In some embodiments, the subject is orally co-administered a drug one hour to twenty-four hours after implantation of the implantable delivery device. In some embodiments, the subject is orally co-administered a drug one day to seven days after implantation of the implantable delivery device. In some embodiments, the subject is orally co-administered a drug one week to one month after implantation of the implantable delivery device. In some embodiments, the subject is orally co-administered a drug one month to three months after implantation of the implantable delivery device. In some embodiments, the subject is orally co-administered a drug three months to six months after implantation of the implantable delivery device. In some embodiments, the subject is orally co-administered a drug six months to one year after implantation of the implantable delivery device. In some embodiments, the subject is orally co-administered a drug one year to two years after implantation of the implantable delivery device.

In some embodiments, the drug is administered for treatment of a disease or disorder other than type-2 diabetes. In some embodiments, the disease or disorder other than type-2 diabetes is selected from the group consisting of pain, elevated blood levels of cholesterol, heart disease, hypertension, heart attack, stroke or blood clot.

In some embodiments, the drug is a contraceptive administered to prevent conception of a child.

In some embodiments, the drug is selected from the group consisting of acetaminophen, atorvastatin, lisinopril, digoxin, ethinyl estradiol, levonorgestrel, R-warfarin, and/or S-warfarin.

In some embodiments, the drug is a pain reliever, such as acetaminophen.

In some embodiments, the drug is acetaminophen and the ratio of the AUC for co-administered acetaminophen after implantation of the implantable delivery device and during continuous subcutaneous dosing of the GLP-1 analog relative to reference AUC for acetaminophen administered alone is between 1.0 and 1.25 or between 0.75 and 1.25.

In some embodiments, the drug is acetaminophen and the AUC for co-administered acetaminophen (e.g., co-administered within 1, 2 or 4 hours of implantation) and during continuous subcutaneous dosing of the GLP-1 analog are reduced less than 10% or 5% relative to reference AUC for acetaminophen administered alone.

In some embodiments, the drug is acetaminophen and the ratio of the $C_{max}$ for co-administered acetaminophen after implantation of the implantable delivery device and during continuous subcutaneous dosing of the GLP-1 analog relative to reference $C_{max}$ for acetaminophen administered alone is between 1.0 and 1.25 or between 0.75 and 1.25.

In some embodiments, the drug is acetaminophen and the $C_{max}$ for co-administered acetaminophen (e.g., within 1, 2 or 4 hours of implantation) and during continuous subcutaneous dosing of the GLP-1 analog are reduced less than 30%, 20%, 10% or 5% relative to reference $C_{max}$ for acetaminophen administered alone.

In some embodiments, the drug is acetaminophen and the $T_{max}$ for co-administered acetaminophen (e.g., within 1, 2 or 4 hours of implantation) and during continuous subcutaneous dosing of the GLP-1 analog is increased by less than 2 hours or 1 hour relative to reference $T_{max}$ for acetaminophen administered alone.

In some embodiments, the drug is an oral contraceptive, such as ethinyl estradiol and/or levonorgestrel. In some embodiments, the oral contraceptive is a combination of ethinyl estradiol and levonorgestrel (e.g., Levora®, 35 mcg ethinyl estradiol plus 150 mcg levonorgestrel).

In some embodiments, the drug is ethinyl estradiol and/or levonorgestrel and the ratio of the AUC for co-administered ethinyl estradiol and/or levonorgestrel after implantation of the implantable delivery device and during continuous subcutaneous dosing of the GLP-1 analog relative to reference AUC for ethinyl estradiol and/or levonorgestrel administered alone is between 0.75 and 1.25 or between 0.75 and 1.50.

In some embodiments, the drug is ethinyl estradiol and/or levonorgestrel and the ratio of the $C_{max}$ for co-administered ethinyl estradiol and/or levonorgestrel after implantation of the implantable delivery device and during continuous subcutaneous dosing of the GLP-1 analog relative to reference $C_{max}$ for ethinyl estradiol and/or levonorgestrel administered alone is between 0.75 and 1.25 or between 0.75 and 1.50.

In some embodiments, the drug is ethinyl estradiol and/or levonorgestrel and the $C_{max}$ for co-administered ethinyl estradiol and/or levonorgestrel (e.g., within 1, 2 or 4 hours of implantation) and during continuous subcutaneous dosing of the GLP-1 analog are reduced less than 30%, 20%, 10% or 5% relative to reference $C_{max}$ for ethinyl estradiol and/or levonorgestrel administered alone.

In some embodiments, the drug is ethinyl estradiol and/or levonorgestrel and the $T_{max}$ for co-administered ethinyl estradiol and/or levonorgestrel (e.g., within 1, 2 or 4 hours of implantation) and during continuous subcutaneous dosing of the GLP-1 analog is increased less than 3 hours, 2 hours or 1 hour relative to reference $T_{max}$ for ethinyl estradiol and/or levonorgestrel administered alone.

In some embodiments, the drug is for the treatment or prevention of elevated blood levels of cholesterol. In some embodiments, the drug is a statin. In some embodiments, the drug is atorvastatin.

In some embodiments, the drug is atorvastatin and the ratio of the AUC for co-administered atorvastatin after implantation of the implantable delivery device and during continuous subcutaneous dosing of the GLP-1 analog relative to reference AUC for atorvastatin administered alone is between 1.0 and 1.25 or between 1.0 and 1.50.

In some embodiments, the drug is atorvastatin and the ratio of the $C_{max}$ for co-administered atorvastatin after implantation of the implantable delivery device and during continuous subcutaneous dosing of the GLP-1 analog relative to reference $C_{max}$ for atorvastatin administered alone is between 1.0 and 1.5 or between 1.0 and 1.75.

In some embodiments, the drug is for the treatment or prevention of hypertension and/or heart disease. In some embodiments, the drug is digoxin.

In some embodiments, the drug is digoxin and the ratio of the AUC for co-administered digoxin after implantation of the implantable delivery device and during continuous subcutaneous dosing of the GLP-1 analog relative to reference AUC for digoxin administered alone is between 1.0 and 1.25 or between 1.0 and 1.50.

In some embodiments, the drug is digoxin and the ratio of the $C_{max}$ for co-administered digoxin after implantation of the implantable delivery device and during continuous subcutaneous dosing of the GLP-1 analog relative to reference $C_{max}$ for digoxin administered alone is between 1.0 and 1.25 or between 1.0 and 1.50.

In some embodiments, the drug is an angiotensin converting enzyme (ACE) inhibitor. In some embodiments, the drug is lisinopril.

In some embodiments, the drug is lisinopril and the ratio of the AUC for co-administered lisinopril after implantation of the implantable delivery device and during continuous subcutaneous dosing of the GLP-1 analog relative to reference AUC for lisinopril administered alone is between 1.5 and 2.0 or between 1.0 and 2.0.

In some embodiments, the drug is lisinopril and the ratio of the $C_{max}$ for co-administered lisinopril after implantation of the implantable delivery device and during continuous subcutaneous dosing of the GLP-1 analog relative to reference $C_{max}$ for lisinopril administered alone is between 1.25 and 1.75 or between 1.0 and 2.0.

In some embodiments, the drug is for the treatment or prevention of a heart attack, stroke, and/or blood clot. In some embodiments, the drug is an anticoagulant. In some embodiments, the drug is R-warfarin and/or S-warfarin.

In some embodiments, the drug is R-warfarin and/or S-warfarin and the ratio of the AUC for co-administered R-warfarin and/or S-warfarin after implantation of the implantable delivery device and during continuous subcutaneous dosing of the GLP-1 analog relative to reference AUC for R-warfarin and/or S-warfarin administered alone is between 1.0 and 1.25 or between 0.75 and 1.5.

In some embodiments, the drug is R-warfarin and/or S-warfarin and the ratio of the $C_{max}$ for co-administered R-warfarin and/or S-warfarin after implantation of the implantable delivery device and during continuous subcutaneous dosing of the GLP-1 analog relative to reference $C_{max}$ for R-warfarin and/or S-warfarin administered alone is less than 1.5 or 1.25.

In some embodiments, the drug is co-administered without dose adjustment. In other words, the normally prescribed dose for the drug is not changed after implantation of the delivery device and during continuous subcutaneous dosing of the GLP-1 analog.

In some embodiments, the drug is self-administered by the subject. In other words, the drug, either prescribed by a physician or obtained as an over-the-counter drug, is taken orally by the subject.

In another aspect, the present invention provides a method comprising administering to a subject, via an implantable delivery device, a continuous subcutaneous dose of glucagon-like peptide-1 (GLP-1) analog, without providing a substantial delay in a rate of gastric emptying in the subject, following administration, relative to the rate of gastric emptying for the subject prior to administration.

In another aspect, the present invention provides a drug for use in a method of treatment of a subject (e.g., a patient suffering from T2D and/or obesity and/or in need of weight loss), the method comprising administering to the subject (e.g., patient), via an implantable osmotic delivery device, a continuous subcutaneous dose of a glucagon-like peptide-1 (GLP-1) analog without providing a substantial delay in a rate of gastric emptying in the subject, following administration, relative to the rate of gastric emptying for the subject prior to administration.

In some embodiments, the method provides less than 20% delay in the rate of gastric emptying in the subject, following administration, relative to the rate of gastric emptying for the subject prior to administration. In some embodiments, the method provides less than 10%, 5% or 1% delay in the rate of gastric emptying in the subject, following administration, relative to the rate of gastric emptying for the subject prior to administration.

In some embodiments, the method provides no substantial delay in the rate of gastric emptying in the subject, between 5 and 29 days following administration, relative to the rate of gastric emptying for the subject prior to administration. In some embodiments, the method provides no substantial delay in a rate of gastric emptying in the subject, between 1 day and 1 week, between 1 day and 2 weeks, or between 1 day and 1 month, following administration, relative to the rate of gastric emptying for the subject prior to administration. In some embodiments, the method provides no substantial delay in a rate of gastric emptying in the subject, during continuous subcutaneous delivery (e.g., during three, six, twelve, or twenty-four month administration period) of a GLP-1 analog such as exenatide (e.g. ITCA-650 at 20 μg/day exenatide or ITCA-650 60 μg/day exenatide).

In some embodiments, the method provides no substantial delay in the fasting rate of gastric emptying. Fasting conditions (e.g., those within a fasting period of at least 24, 12, 8, 6, 4 or 2 hours without consumption of food or a meal) correspond to those well known to those of ordinary skill in the art. As used herein, the term "substantial" corresponds to less than 20%, less than 10%, less than 5% or less than 1%.

In some embodiments, the method provides no substantial (e.g., less than 20%, less than 10%, less than 5% or less than 1%) delay in the post-prandial rate of gastric emptying. Post-prandial conditions (e.g., those within a feeding period of 12, 8, 6, 4, 2 or 1 hour(s), during which food or a meal was consumed) correspond to those well known to those of ordinary skill in the art.

In another aspect, the present invention provides a method comprising administering to a subject, via an implantable delivery device, a continuous subcutaneous dose of glucagon-like peptide-1 (GLP-1) analog without effecting a substantial reduction in glucagon concentration in blood of the subject, following administration, relative to glucagon concentration in blood of the subject prior to administration.

In another aspect, the present invention provides a drug for use in a method of treatment of a subject (e.g., a patient suffering from T2D and/or obesity and/or in need of weight loss), the method comprising administering to the subject (e.g., patient), via an implantable osmotic delivery device, a continuous subcutaneous dose of a glucagon-like peptide-1 (GLP-1) analog without providing a substantial reduction in glucagon concentration in blood of the subject, following administration, relative to glucagon concentration in blood of the subject prior to administration.

In some embodiments, the method provides less than 20% reduction in glucagon concentration in blood of the subject, following administration, relative to glucagon concentration in blood of the subject prior to administration. In some embodiments, the method provides less than 10%, 5% or 1% reduction in glucagon concentration in blood of the subject, following administration, relative to glucagon concentration in blood of the subject prior to administration.

In some embodiments, the method provides no substantial reduction in glucagon concentration in blood of the subject, between 5 and 29 days following administration, relative to glucagon concentration in blood of the subject prior to administration. In some embodiments, the method provides no substantial reduction in glucagon concentration in blood of the subject, between 1 day and 1 week, between 1 day and 2 weeks, or between 1 day and 1 month, following administration, relative to glucagon concentration in blood of the subject prior to administration. In some embodiments, the method provides no substantial reduction in glucagon concentration in blood of the subject, during continuous subcutaneous delivery (e.g., during three, six, twelve, or twenty-four month administration period) of a GLP-1 analog such as exenatide (e.g. ITCA-650 at 20 µg/day exenatide or ITCA-650 60 µg/day exenatide).

In some embodiments, the method provides no substantial (e.g., less than 20%, less than 10%, less than 5% or less than 1%) reduction in fasting glucagon concentration.

In some embodiments, the method provides no substantial (e.g., less than 20%, less than 10%, less than 5% or less than 1%) reduction in post-prandial glucagon concentration.

In some embodiments, the GLP-1 analog is exenatide. In some embodiments, the GLP-1 analog is other than exenatide. In some embodiments, the GLP-1 analog is selected from the group consisting of Ozempic® (semaglutide), Victoza® (liraglutide), Adlyxin® (lixisenatide), Tanzeum® (albiglutide), and Trulicity® (dulaglutide). In some embodiments, the GLP-1 analog is Ozempic® (semaglutide). In some embodiments, the GLP-1 analog is Victoza® (liraglutide). In some embodiments, the GLP-1 analog is Adlyxin® (lixisenatide). In some embodiments, the GLP-1 analog is Trulicity® (dulaglutide). In some embodiments, the GLP-1 analog is Tanzeum® (albiglutide).

In some embodiments, the GLP-1 analog is administered for treatment of a metabolic disorder. In some embodiments, the GLP-1 analog is administered for treatment of a type 2 diabetes mellitus. In some embodiments, the GLP-1 analog is administered for treatment of obesity. In some embodiments, the GLP-1 analog is administered for effecting weight loss in the subject.

In some embodiments, the subject is administered a dose of 20 µg/day ITCA-650. In some embodiments, the subject is administered a dose of 60 µg/day ITCA-650.

In some embodiments, the subject is human.

EXEMPLIFICATION

The following examples are put forth to provide those of ordinary skill in the art with a complete disclosure and description of how to practice the present invention, and are not intended to limit the scope of what the inventors regard as the invention. Efforts have been made to ensure accuracy with respect to numbers used (e.g., amounts, concentrations, and percent changes) but some experimental errors and deviations may remain.

General Methods for Examples 1-3

Data source: Data relating to the Meal Tolerance Test (MTT) were derived from the evaluable cohort, comprising all randomized subjects who completed Day −1 (pre-treatment) MTT assessments and completed all pharmacodynamic assessments for at least one of the three scheduled post-treatment MTT assessments. One subject from the originally randomized cohort of n=45 that completed pre-treatment MTT did not complete any post-treatment MTT assessments and was excluded from the evaluable cohort. Thus, there were 44 subjects in the evaluable population: 12 subjects in the ITCA 650 10 mcg/day group, 11 subjects in the ITCA 650 20 mcg/day group, 10 subjects in the ITCA 650 40 mcg/day group, and 11 subjects in the ITCA 650 80 mcg/day group. Of all scheduled MTT assessments, 43/44 (98%) were completed on Day 5, 37/44 (84%) on Day 15, and 42/44 (95%) on Day 29.

Data from SAS dataset "LB" containing all lab values were downloaded into an Excel file (2013 v15 Office 365 module) for sorting of plasma glucose, insulin and glucagon values by treatment group, subject, visit number, and time within the meal tolerance assessment (there being 7 values, including 1 pre-meal and 6 post-meal, for each analyte). Assembled Excel tables were imported into GraphPad Prism (v7.02.185, www.graphpad.com, San Diego, Calif.) for graphical analysis.

Values missing from a time series, where there was a preceding and following value, were imputed by linear interpolation. Where an initial value in a time series was missing, it was imputed as the median of the values present at that time point. Since initial values were typically low, the bias from this treatment is likely negligible. The number of values imputed by this method was 11 (of a final matrix of 3611 values; 0.3%).

Example 1. ITCA-650 and Gastric Emptying Rate

Changes in plasma glucose result from differences in rate of appearance (Ra) and rate of disappearance (Rd; disposal). Rd is primarily an insulin-driven flux. Ra is comprised of meal-related appearance, as well as glucose from endogenous sources, such as hepatic gluconeogenesis. Because insulin is initially low, and takes time to reach its cellular target in the fat and muscle interstitium, and because it takes time to exert its cellular effect of mobilizing GLUT4 transporters, most of the meal-related changes in the initial 30-60 minutes after a meal relate to rates of appearance. Agents that slow the emptying of the stomach, including amylin agonists, CCK agonists, PYY agonists and GLP-1 agonists, dose-dependently suppress glucose rise following test meals, regardless of the effect of such agents to modify insulin secretion. When glucose is the test meal (OGTT), simultaneously measured gastric emptying correlated highly with changes in plasma glucose at 30 min (Horowitz, M., M. A. Edelbroek, J. M. Wishart and J. W. Straathof (1993). "Relationship between oral glucose tolerance and gastric emptying in normal healthy subjects." Diabetologia 36(9): 857-862). Changes in plasma glucose from pre-meal to 30 minutes post-meal ($\Delta Glucose_{30}$) were explored as evidence of an effect of ITCA-650 on gastric emptying.

Methods

Changes ($\Delta Glucose_{30}$) were related to those observed before treatment, and the difference ($\Delta\Delta Glucose_{30}$) explored as a function of duration of treatment and exenatide infusion rate. Dose responses were fitted to a 3-parameter sigmoid (GraphPad Prism v7; www.graphpad.com; San Diego Calif.), and the fits constrained so that the dose-responses from each of the 3 durations of treatment (5, 15 and 29 days) shared a common $ED_{50}$.

Results

Figure 1:
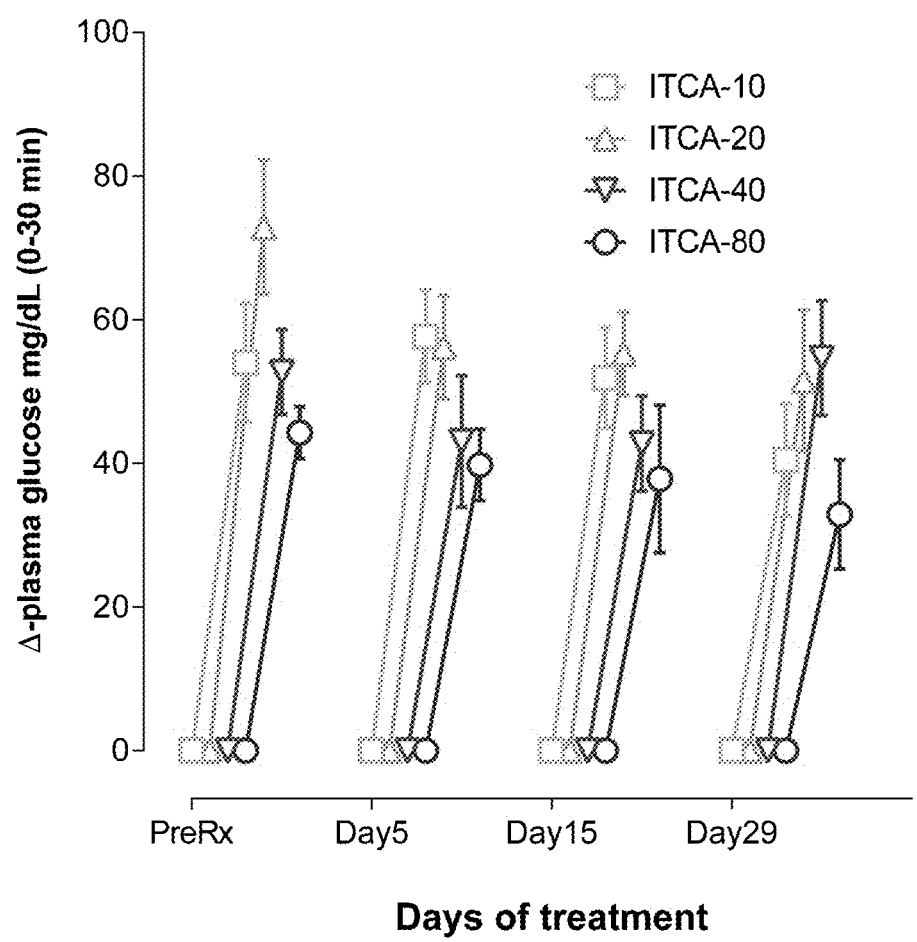

The $\Delta Glucose_{30}$ for each dose group, before and after 5, 15 and 29 days of treatment are shown in FIG. 1 which illustrates 0-30-minute increments in plasma glucose during test meals for 10-, 20-, 40- and 80 µg/day exenatide treatments, measured before and after 5, 15, and 29 days of treatment. Symbols are group means of individual increments±standard error of the mean (SEM).

Figure 2:
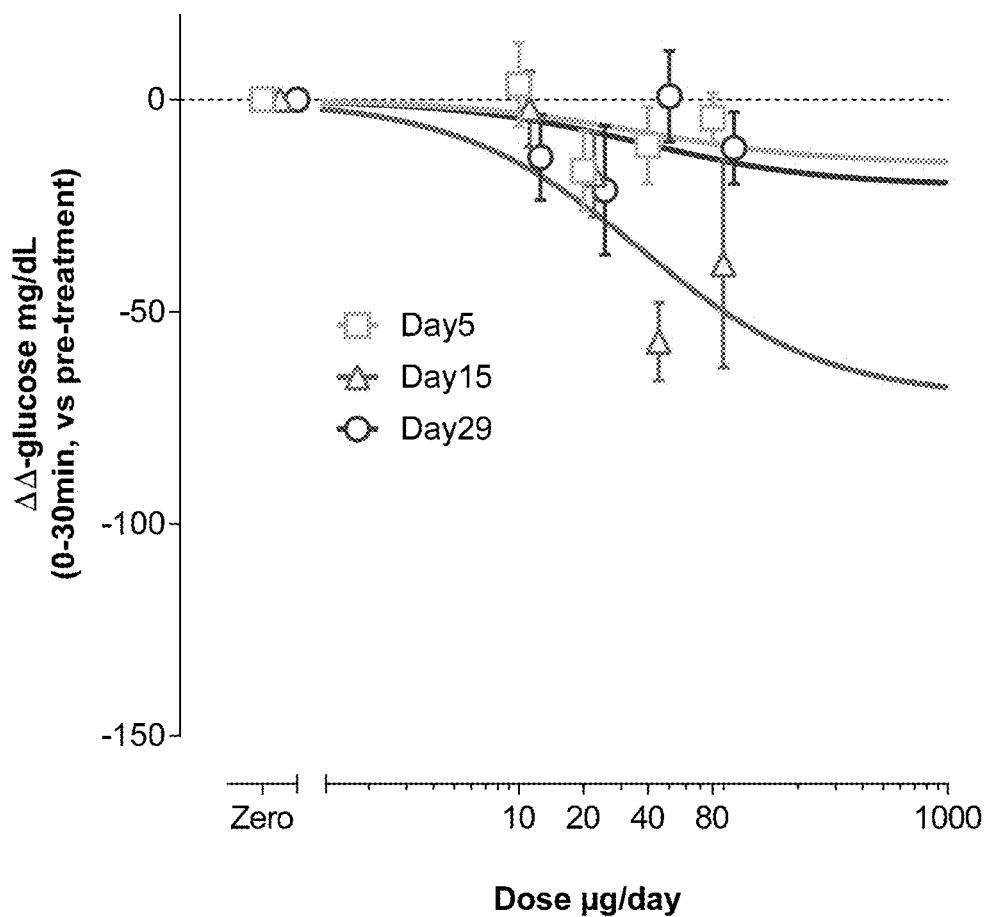

The $\Delta\Delta Glucose_{30}$, representing the pretreatment-referenced change, is plotted as a function of dose in FIG. 2. A dose-dependency of $\Delta Glucose_{30}$ was suggested after 15 days of treatment ($r^2$ 0.22), but this was not apparent either before, at Day 5 ($r^2$ 0.02) or after, at Day 29 ($r^2$ 0.01).

FIG. 2 illustrates dose-responses for 30-minute changes in glucose concentrations during test meals relative to pre-treatment values. Curves for Days 5, 15 and 29 are 3-parameter sigmoids constrained to share a common $ED_{50}$. Symbols are group means of individual values±SEM.

Exemplary Conclusions

Changes in plasma glucose after a test meal, as shown in FIG. 1, were of the order of 40 to 60 mg/dL 30 minutes after the meal. The increments after treatment were similar to the values recorded in the same subjects prior to treatment.

A dose-dependency of changes relative to those observed prior to treatment was suggested after 15 days of treatment, but was not present after either 5 or 29 days of treatment.

The magnitude of suppression of post-meal glucose increments, where present, was small compared to another study in non-diabetic subjects where changes in post-meal glucose were measured following s.c. bolus injections of 5 or 19 µg exenatide (Linnebjerg, H., P. A. Kothare, Z. Skrivanek, A. de la Pena, C. Ernest, M. Atkins and M. E. Trautmann (2004). "Exenatide: postprandial glucose pharmacodynamics at various dosing times relative to a meal in patients with type 2 diabetes." Diabetologia 47(suppl 1): A280. Abstract 776). The exenatide dose-dependency observed in that study, and in another where glucose was the test meal (OGTT) (Kolterman, O. G., J. B. Buse, M. S. Fineman, E. Gaines, S. Heintz, T. A. Bicsak, K. Taylor, D. Kim, M. Aisporna, Y. Wang and A. D. Baron (2003). "Synthetic exendin-4 (exenatide) significantly reduces postprandial and fasting plasma glucose in subjects with type 2 diabetes." J Clin Endocrinol Metab 88(7): 3082-3089) was not a consistent feature in the current study.

Without being bound by theory, it thus appears that the effect of bolus injections of exenatide on post-prandial glucose changes may be, at least in part, a consequence of inhibition of gastric emptying. By contrast, gastric emptying does not appear to be inhibited upon chronic infusion of exenatide, as in the present study.

Example 2. ITCA-650 and Post-Prandial Glucagon Secretion

Exaggeration of glucagon secretion in response to protein-containing meals has been reported in subjects with insulinopenic diabetes, including severe type 2 diabetes (Raskin, P., I. Aydin, T. Yamamoto and R. H. Unger (1978). "Abnormal alpha cell function in human diabetes: the response to oral protein." Am J Med 64(6): 988-997) and has been implicated in the pathogenesis of disturbed metabolism (Unger, R. H. (1978). "Role of glucagon in the pathogenesis of diabetes: the status of the controversy." Metabolism 27(11): 1691-1709).

Methods

Plasma glucagon concentration profiles during meal tolerance tests were plotted as a function of treatment (10-, 20-, 40- and 80-µg exenatide per day) and as a function of duration of treatment (pre-treatment and after 5, 15 and 29 days of treatment). Means and SEM of the data at each of these 16 conditions (4 treatments×4 durations) was derived from data present with no imputation of missing values. Numbers of values present ranged from 7-12.

Data were also analyzed as absolute change from baseline (Δglucagon), and plotted as for glucagon for each of the 16 conditions.

Area under the curve for total glucagon ($AUC_{0-3}$) and for change in glucagon from 0 min during the MTT ($\Delta AUC_{0-3}$) were derived by trapezoidal interpolation and were each plotted as a function of duration of treatment for each of the treatment groups.

Results

Figure 3:
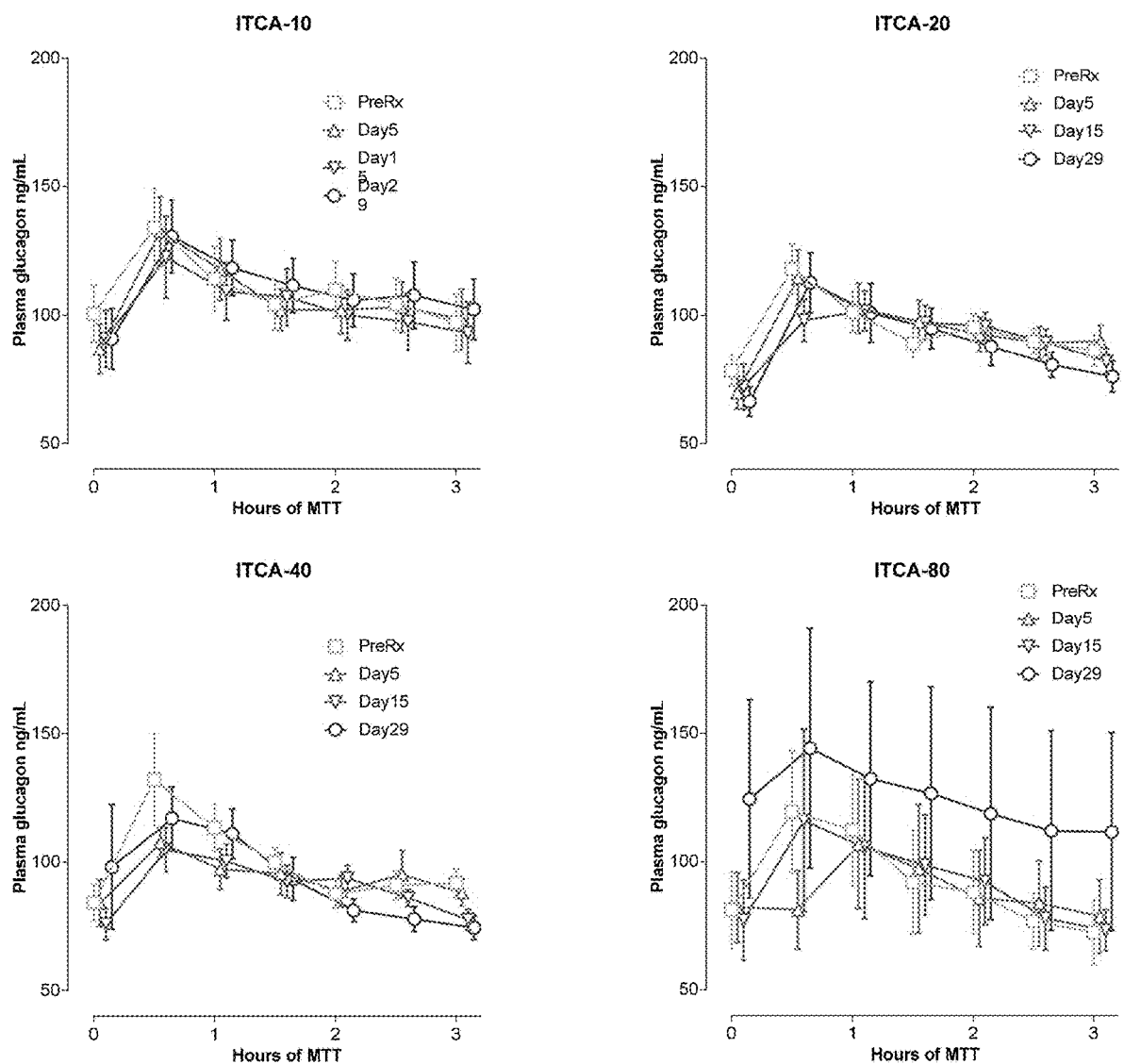
FIG. 3 depicts graphs illustrating plasma glucagon profiles during meal tolerance tests plotted according to duration of treatment (different symbols and colors) for each of the 4 dose groups (separate panels). Symbols are means±SEM for data present at each condition.

Plasma glucagon profiles during meal tolerance tests are plotted as a function of duration of treatment, for each dose group in separate panels, in FIG. 3. Plasma glucagon profiles were typically maximal 30 min after the test meal, declining gradually thereafter. The profiles were similar between all 16 treatments shown. A high initial baseline and high SEM in the 80-µg/day treatment group at Day 29 was driven by 2 subjects with values 4- to 6-fold higher than values in the other 15 treatment conditions, and may not be reliable.

FIG. 3 illustrates plasma glucagon profiles during meal tolerance tests plotted according to duration of treatment (different symbols and colors) for each of the 4 dose groups (separate panels). Symbols are means±SEM for data present at each condition.

Figure 4:
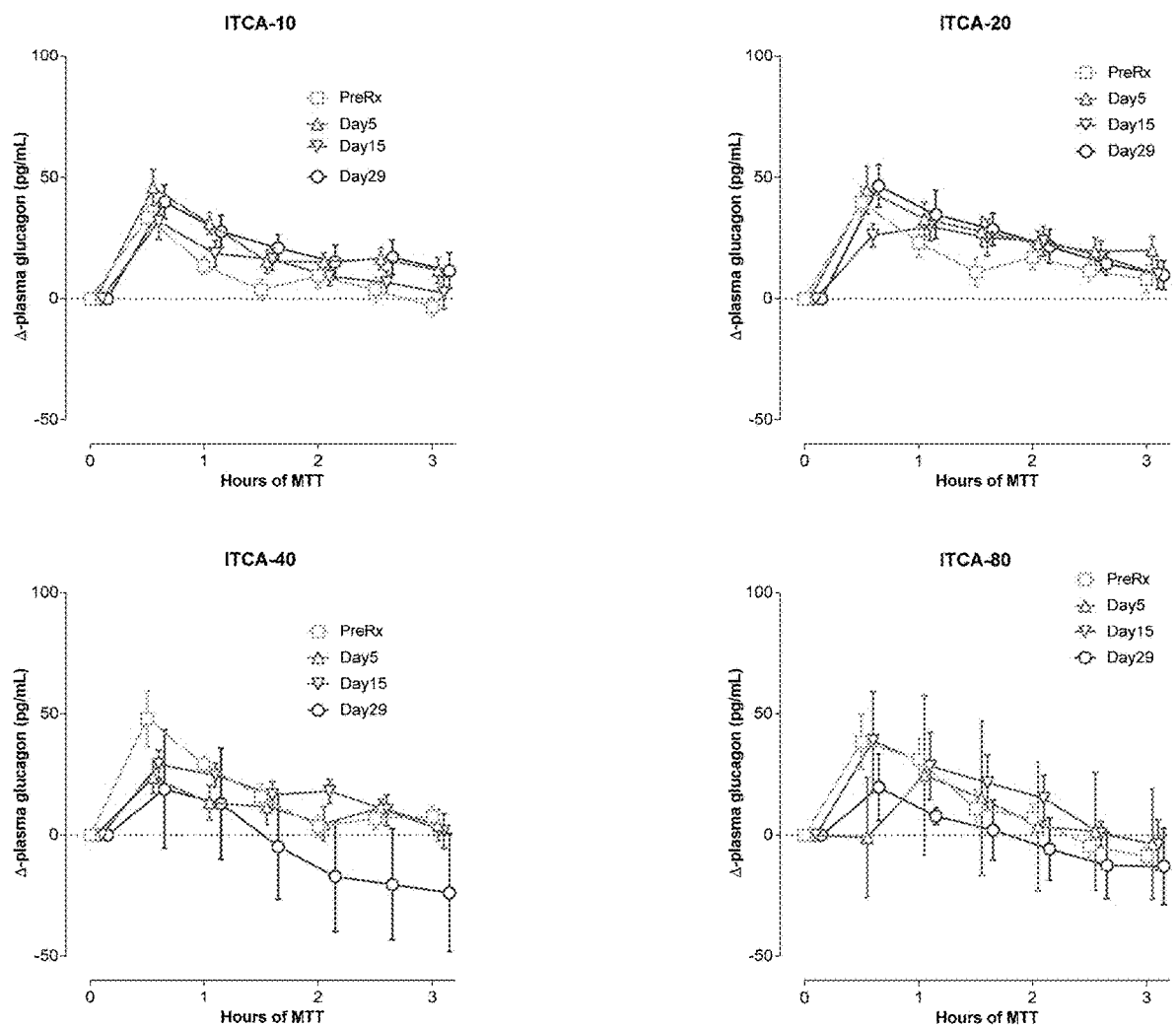
FIG. 4 depicts graphs illustrating changes in plasma glucagon concentration from pre-meal values during a test meal. Symbols, colors and layout have the same meanings as those in FIG. 3.

Change in plasma glucagon from pre-meal values is plotted in FIG. 4. Profiles were generally similar for each of the 16 conditions. While changes appeared less for 40- and 80-µg/day treatments at Day 29, there was no indication of a suppression of post-prandial glucagon at Day 15. These measures may be unreliable for the reasons addressed above.

FIG. 4 illustrates changes in plasma glucagon concentration from pre-meal values during a test meal. Symbols, colors and layout have the same meanings as those in FIG. 3.

Figure 5:
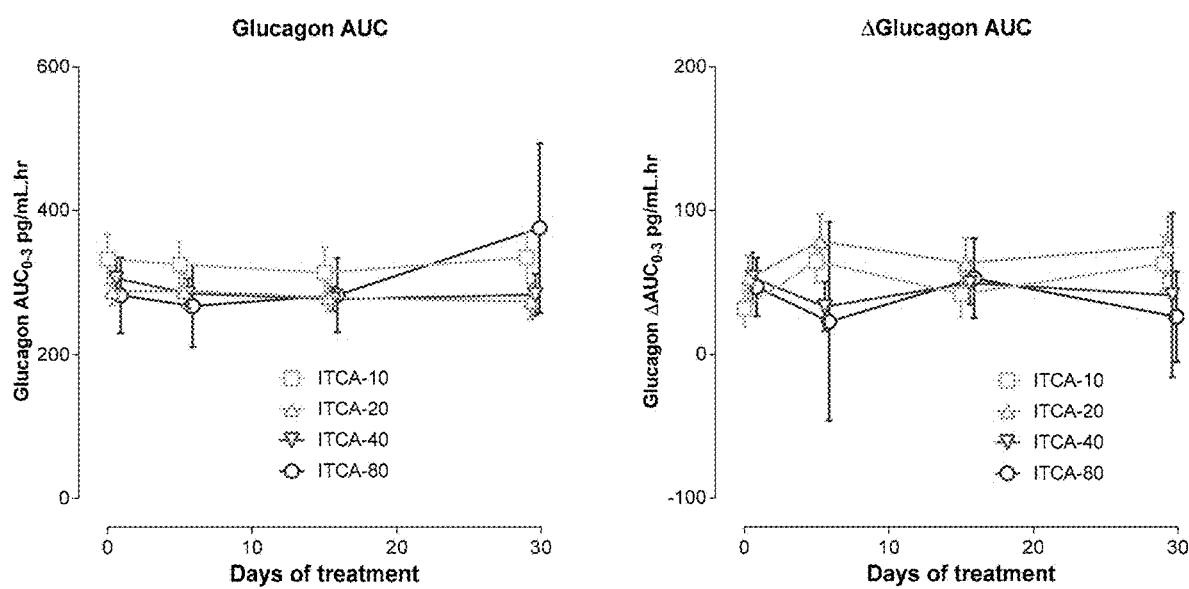
FIG. 5 depicts graphs illustrating integrated glucagon concentrations (left panel) or glucagon changes (right panel) during Meal Tolerance Test (MTT) as a function of duration of treatment for each dose group.

The AUC for absolute glucagon concentrations and for post-meal change in concentration graphed in FIGS. 3 and 4, are plotted in FIG. 5 as a function of duration of treatment for each of the 4 dose groups.

By neither analysis does there appear to be a change from pre-treatment $AUC_{0-3}$ or $\Delta AUC_{0-3}$ at any duration of treatment.

FIG. 5 illustrates integrated glucagon concentrations (left panel) or glucagon changes (right panel) during Meal Tolerance Test (MTT) as a function of duration of treatment for each dose group.

Exemplary Conclusions

The data obtained for continuous subcutaneous infusions of exenatide with ITCA-650 do not support suppression of post-prandial glucagon as a significant mechanism underlying its glucose-lowering effect. These observations contrast with those of Kolterman et al. (Kolterman, et al., J Clin Endocrinol Metab 2003) where bolus subcutaneous injections of 1-µg/kg exenatide abrogated the ~70 pg/mL increase in plasma glucagon 1 hour after a test meal. Since meal-stimulated glucagon secretion may be at least partially moderated by changes in gastric emptying, the absence of effect here may be consistent with an absence of effect of continuously delivered exenatide on gastric emptying, as described above.

Example 3. ITCA-650 and Glucose-Stimulated Insulin Secretion

The ability of glucagon-like peptide-1 was reported in 1987 (Mojsov, S., G. C. Weir and J. F. Habener (1987). "Insulinotropin: glucagon-like peptide I (7-37) co-encoded in the glucagon gene is a potent stimulator of insulin release in the perfused rat pancreas." J Clin Invest 79(2): 616-619) to stimulate insulin secretion in a glucose-dependent manner, having no effect at low plasma glucose concentrations. Every GLP-1 agonist reported since then appears to have this property. We therefore sought to determine whether the relationship between resulting plasma insulin concentrations and simultaneously determined plasma glucose concentrations in the present study supported such a mechanism.

A challenge arises in determining the [insulin]/[glucose] relationship in subjects with type 2 diabetes because the natural history of T2D places subjects in different zones of the [insulin]*[glucose] plane, according to the stage of their disease. Proposed by Reaven and Miller (Reaven, G. M. and R. Miller (1968). "Study of the relationship between glucose and insulin responses to an oral glucose load in man." Diabetes 17(9): 560-569) based upon cross-sectional data, and affirmed by Saad et al. (Saad, M. F., W. C. Knowler, D. J. Pettitt, R. G. Nelson, D. M. Mott and P. H. Bennett (1989). "Sequential changes in serum insulin concentration during development of non-insulin-dependent diabetes." Lancet 1(8651): 1356-1359) based upon longitudinal data, the progression begins with amplification of insulin secretion, accompanied by moderate dysglycemia, as insulin resistance becomes established. This is followed in a subset of individuals by florid hyperglycemia, as insulin secretory capacity fails, likely due to islet destruction by amyloid. The result is an inverted U-shaped distribution of [insulin]/[glucose] data pairs, shown for the 2-hour post-OGTT timepoint in FIG. 6A. Individuals tend to follow the trajectories of the yellow arrows as they progress from normal, to IGT, to T2D. FIG. 6B, shows [insulin]/[glucose] diagrams from the MTT in T2D subjects prior to treatment with 80-μg/day exenatide. The progression mapped in FIG. 6A is apparent in the [insulin/[glucose] diagram from the current study in FIG. 6B. The sequence of serial measurements is indicated by the direction of the arrows. For example, subjects 31-047 and 31-044 show a vigorous insulin response with modest increases in glucose following the test meal, consistent with the insulin resistant phase of progression. In contrast, subjects 32-021 and 33-026 show large glycemic excursions and only meager insulin responses, consistent with the secretory failure phase of disease progression. Another feature of the [insulin]/[glucose] trajectories in the current study is hysteresis, wherein the path of descending data pairs is different from that of ascending data pairs. Accommodation of these features is addressed in the analytic methods.

FIG. 6A (left), redrawn from Saad et al., maps the changing [insulin] vs [glucose] relationship during the progression from normal glucose tolerance to T2D. FIG. 6B (right) exemplifies the diverse [insulin] vs [glucose] relationships in the current study.

Methods

The effect of glucose upon insulin secretion was quantified as the slope of the [insulin] vs [glucose] relationship, as exemplified in FIG. 6B. The slope was estimated by linear regression, the intersection with the X-axis being unique for each subject.

Because of factors such as the time lag for induction of insulin effect, and non-instantaneous clearance of secreted insulin, only data pairs for the ascending part of the hysteresis loop were used in the analysis. These segments are signified by the thick lines in FIG. 6B. Thus, subjects 31-044 and 31-047 yielded similar slopes. Subjects 32-021 and 32-032 had similar slopes but different intersections with the X-axis. Subject 33-026 had the lowest slope.

Such diagrams were analyzed for each subject for each meal tolerance test (pre-treatment and after 5, 15 and 29 days of treatment). Observation suggested that the X-intercept (glucose concentration below which insulin was not secreted) was essentially unchanged by the treatments, so linear regression was constrained to yield a best-fitting fixed X-intercept for all tests in a given subject. Families of up to 4 [insulin] vs [glucose] relationships were fitted to a straight line where the X-intercept was shared, but slopes were able to vary. This was done by fitting the equation [glucose]=m.[insulin]+c (actually the inverse of slopes in FIG. 6B) using least squares interaction in the non-linear module of Prism v7 (www.graphpad.com; San Diego, Calif.), and retrieving the reciprocal of m as the [insulin] vs [glucose] slope.

Because pre-treatment slopes varied widely between individuals, slopes derived during treatment were expressed as a multiple of the pre-treatment slope. Negative slopes, comprising 4/216 (1.8%) of those derived, were disregarded.

Results

The slope of the [insulin]/[glucose] relationship increased from 1.7-fold with 10 μg/day treatment up to 3.45-fold with 80 μg/day treatment. The slope was near maximal after a week (tau 3.5 days), as shown in FIG. 7.

FIG. 7 illustrates multiples above pre-treatment baseline of best fitting [insulin]×[glucose] slopes. The curves are the best fitting exponential association as a function of duration of treatment.

The relative increments in slope after 29 days were analyzed by dose group to obtain the dose response relationship shown in FIG. 8. The sigmoid fit suggests the $ED_{50}$ for the slope change is ~40 μg/day.

FIG. 8 illustrates dose response for the effect of ITCA-650 to increase slope of the [insulin]/[glucose] relationship.

Exemplary Conclusions

Analysis of treatment-related changes in [insulin] vs [glucose] relationships during meal tolerance tests are indicative of an insulinotropic effect of ITCA-650. Dose response analysis indicates this effect is dose dependent, and that the $ED_{50}$ may be near or below indicated doses.

Example 4. ITCA 650 and the Pharmacokinetics (PK) of Acetaminophen (APAP) and Other Commonly Co-Administered Drugs Methods Thirty-three (33) healthy volunteers were enrolled in a sequential, open-label study to assess the effect of ITCA 650 on the PK of APAP 1000 mg, and on the PK and pharmacodynamics (PD) of 4 commonly co-administered drugs: atorvastatin (40 mg), lisinopril (20 mg), digoxin (0.5 mg), and warfarin (25 mg) administered as a cocktail. See FIG. 9. APAP, a marker of gastric emptying, was administered on Day (D)1 followed by the cocktail on D2. ITCA 650 20 mcg/day was placed on D6 and replaced by ITCA 650 60 mcg/day on D20. APAP was administered again on D27 and the cocktail on D28. ITCA 650 60 mcg/day was removed on D32. Serial PK (exenatide; co-administered drugs) and PD (PT-INR) samples were collected.

Results

There was minimal effect of ITCA 650 on gastric emptying rate as seen in FIG. 9 with the 90% CI of the LS means ratio for AUC between 80-125%. There were no changes in digoxin and warfarin PK or INR. While there were moderate increases in lisinopril and atorvastatin exposures, there were no clinically relevant effects on safety and tolerability of either drug.

Exemplary Conclusion

There was no substantial effect of ITCA 650 on gastric emptying and no dosage adjustment is deemed necessary when ITCA 650 is co-administered with these commonly used drugs.

Example 5. ITCA 650 and the PK and Pharmacodynamics (PD) of a Combination Oral Contraceptive (OC)

Methods

Twenty-eight (28) healthy premenopausal women on a stable regimen of an OC participated in a randomized, double-blind, placebo-controlled, 2-period crossover study. The effect of ITCA 650 on the steady-state PK of ethinyl estradiol (EE) and levonorgestrel (LNG) from Levora® (OC) were evaluated. The study included a 2-week run-in on Levora and 2 treatment periods of 28 days each. In Period 1, ITCA 650 20 mcg/day or ITCA placebo was placed on Day (D) 1 followed by removal and replacement with ITCA 650 60 mcg/day or ITCA placebo on D15. Subjects were crossed over to the alternative treatment and procedures were repeated in Period 2. The OC was administered daily through D28 of each period. Serial samples for PK analysis of exenatide, EE, LNG, and pharmacodynamics (LH, FSH, and progesterone) analysis were collected.

Results

No effect of ITCA 650 60 mcg/day on EE and LNG PK was observed (FIG. 10). The 90% CIs of the geometric LS mean treatment ratios for $AUC_{ss}$ and $C_{max,ss}$ were contained within the equivalence limits of 80% to 125%. Levels of LH, FSH, and progesterone were unaffected by the administration of ITCA 650.

Exemplary Conclusion

No dose adjustments are required when ITCA 650 is administered with Levora, a combination OC.

Example 6. Drug Interaction Studies—Potential for Exenatide to Influence the Pharmacokinetics of Other Drugs In clinical pharmacology studies ITCA-650 did not affect the pharmacokinetics of the orally administered medications to a clinically relevant degree. FIG. 11 illustrates pharmacokinetic parameters and their 90% confidence intervals (CI), indicating the magnitude of these interactions. No dose adjustment is recommended for any of the evaluated co-administered medications. ITCA-650 had a minimal effect on acetaminophen pharmacokinetics indicating that it has a minimal effect on gastric emptying. ITCA-650 did not significantly alter the pharmacodynamic effects of warfarin as measured by the international normalized ratio (INR).

We claim:

1. A method comprising administering to a subject in need thereof, via an implantable delivery device, a continuous subcutaneous dose of glucagon-like peptide-1 (GLP-1) analog, wherein the subject is orally co-administered a drug after implantation of the implantable delivery device and during continuous subcutaneous dosing of the GLP-1 analog, and wherein the drug is administered without dose adjustment for treatment of a disease or disorder other than type-2 diabetes.

2. The method of claim 1, wherein the disease or disorder other than type-2 diabetes is selected from the group consisting of pain, elevated blood levels of cholesterol, heart disease, hypertension, heart attack, stroke or blood clot.

3. The method of claim 1, wherein the drug is administered to prevent conception of a child.

4. The method of claim 1, wherein the drug is selected from the group consisting of acetaminophen, atorvastatin, lisinopril, digoxin, ethinyl estradiol, and levonorgestrel, R-warfarin, and S-warfarin.

5. The method of claim 1, wherein the drug is a pain reliever.

6. The method of claim 1, wherein the drug is acetaminophen.

7. The method of claim 1, wherein the drug is an oral contraceptive.

8. The method of claim 1, wherein the drug is one or both of ethinyl estradiol and levonorgestrel.

9. The method of claim 1, wherein the drug is for the treatment of elevated blood levels of cholesterol.

10. The method of claim 1, wherein the drug is a statin.

11. The method of claim 1, wherein the drug is atorvastatin.

12. The method of claim 1, wherein the drug is for the treatment or prevention of hypertension and/or heart disease.

13. The method of claim 1, wherein the drug is digoxin.

14. The method of claim 1, wherein the drug is an angiotensin converting enzyme (ACE) inhibitor.

15. The method of claim 1, wherein the drug is lisinopril.

16. The method of claim 1, wherein the drug is for the treatment or prevention of a heart attack, stroke, hypertension or blood clot.

---

SEQUENCE LISTING

<160> NUMBER OF SEQ ID NOS: 1

<210> SEQ ID NO 1
<211> LENGTH: 39
<212> TYPE: PRT
<213> ORGANISM: Heloderma suspectum

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
        35

17. The method of claim 1, wherein the drug is an anticoagulant.

18. The method of claim 1, wherein the drug is R-warfarin and/or S-warfarin.

19. The method of claim 1, wherein the drug is self-administered by the subject.

20. The method of claim 1, wherein the GLP-1 analog is exenatide.

21. The method of claim 1, wherein the GLP-1 analog is other than exenatide.

22. The method of claim 21, wherein the GLP-1 analog is selected from the group consisting of OZEMPIC® (semaglutide), VICTOZA® (liraglutide), ADLYXIN® (lixisenatide); TENZEUM® (albiglutide) and TRULICITY® (dulaglutide).

23. The method of claim 1, wherein the GLP-1 analog is administered for treatment of a metabolic disorder.

24. The method of claim 1, wherein the GLP-1 analog is administered for treatment of a type 2 diabetes mellitus.

25. The method of claim 1, wherein the GLP-1 analog is administered for treatment of obesity.

26. The method of claim 1, wherein the GLP-1 analog is administered for effecting weight loss in the subject.

27. The method of claim 1, wherein the subject is administered a dose of 20 μg/day exenatide.

28. The method of claim 1, wherein the subject is administered a dose of 60 μg/day exenatide.

29. The method of claim 1, wherein the subject is human.

* * * * *